(12) United States Patent
Thomas, Jr. et al.

(10) Patent No.: US 10,450,367 B2
(45) Date of Patent: Oct. 22, 2019

(54) HUMAN ANTIBODIES AGAINST RABIES AND USES THEREOF

(71) Applicant: University of Massachusetts, Boston, MA (US)

(72) Inventors: William D. Thomas, Jr., Dedham, MA (US); Yang Wang, Natick, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/750,716

(22) PCT Filed: Aug. 12, 2016

(86) PCT No.: PCT/US2016/046774
§ 371 (c)(1),
(2) Date: Feb. 6, 2018

(87) PCT Pub. No.: WO2017/027805
PCT Pub. Date: Feb. 16, 2017

(65) Prior Publication Data
US 2019/0002534 A1 Jan. 3, 2019

Related U.S. Application Data

(60) Provisional application No. 62/204,894, filed on Aug. 13, 2015.

(51) Int. Cl.
| | |
|---|---|
| *C07K 16/10* | (2006.01) |
| *A61K 39/12* | (2006.01) |
| *A61P 31/14* | (2006.01) |
| *A61K 39/205* | (2006.01) |
| *A61K 39/00* | (2006.01) |

(52) U.S. Cl.
CPC .............. *C07K 16/10* (2013.01); *A61K 39/12* (2013.01); *A61K 39/205* (2013.01); *A61P 31/14* (2018.01); *A61K 2039/507* (2013.01); *A61K 2300/00* (2013.01); *C07K 2317/21* (2013.01); *C07K 2317/34* (2013.01); *C07K 2317/76* (2013.01); *C12N 2760/20121* (2013.01); *C12N 2760/20134* (2013.01); *C12N 2760/20171* (2013.01)

(58) Field of Classification Search
None
See application file for complete search history.

(56) References Cited

U.S. PATENT DOCUMENTS

| | | |
|---|---|---|
| 2005/0074821 A1 | 4/2005 | Wild, Jr. et al. |
| 2013/0039926 A1* | 2/2013 | Thomas, Jr. ......... A61K 39/205 424/159.1 |
| 2015/0110781 A1 | 4/2015 | Shen et al. |

FOREIGN PATENT DOCUMENTS

| | | |
|---|---|---|
| EP | 0324157 A1 | 7/1989 |
| EP | 0402029 A2 | 12/1990 |

OTHER PUBLICATIONS

International Preliminary Report on Patentability for International Patent Application No. PCT/US2016/046774, dated Feb. 13, 2018 (6 pages).
International Search Report and Written Opinion for International Patent Application No. PCT/US2016/046774, dated Nov. 16, 2016 (10 pages).

* cited by examiner

*Primary Examiner* — Shanon A. Foley
*Assistant Examiner* — Myron G Hill
(74) *Attorney, Agent, or Firm* — Clark & Elbing LLP

(57) ABSTRACT

The invention provides human antibodies against rabies and methods of using the same.

32 Claims, 9 Drawing Sheets

Specification includes a Sequence Listing.

SEQUENCE LISTING

```
<160> NUMBER OF SEQ ID NOS: 28

<210> SEQ ID NO 1
<211> LENGTH: 10
<212> TYPE: PRT
<213> ORGANISM: Homo sapiens

<400> SEQUENCE: 1

Gly Phe Thr Phe Ser Tyr Phe Ala Met His
1               5                   10

<210> SEQ ID NO 2
<211> LENGTH: 16
<212> TYPE: PRT
<213> ORGANISM: Homo sapiens

<400> SEQUENCE: 2

Thr Ile Gly Thr Gly Gly Gly Thr Tyr Tyr Ala Asp Ser Val Lys Gly
```

```
                1               5                  10                 15
```

<210> SEQ ID NO 3
<211> LENGTH: 19
<212> TYPE: PRT
<213> ORGANISM: Homo sapiens

<400> SEQUENCE: 3

```
Cys Ala Arg Asp Asn Ala Leu Arg Ser Phe Asp Trp Leu Phe Tyr Ser
1               5                   10                  15

Phe Asp Tyr
```

<210> SEQ ID NO 4
<211> LENGTH: 12
<212> TYPE: PRT
<213> ORGANISM: Homo sapiens

<400> SEQUENCE: 4

```
Arg Ala Ser Gln Ser Ile Ser Ser Ser Tyr Leu Ala
1               5                   10
```

<210> SEQ ID NO 5
<211> LENGTH: 7
<212> TYPE: PRT
<213> ORGANISM: Homo sapiens

<400> SEQUENCE: 5

```
Gly Ala Ser Ser Arg Ala Thr
1               5
```

<210> SEQ ID NO 6
<211> LENGTH: 8
<212> TYPE: PRT
<213> ORGANISM: Homo sapiens

<400> SEQUENCE: 6

```
Gln Arg Tyr Gly Ser Ser Tyr Thr
1               5
```

<210> SEQ ID NO 7
<211> LENGTH: 25
<212> TYPE: PRT
<213> ORGANISM: Homo sapiens

<400> SEQUENCE: 7

```
Glu Val Gln Leu Val Gln Ser Gly Gly Gly Leu Val His Pro Gly Gly
1               5                   10                  15

Ser Leu Arg Leu Ser Cys Ala Gly Ser
            20                  25
```

<210> SEQ ID NO 8
<211> LENGTH: 14
<212> TYPE: PRT
<213> ORGANISM: Homo sapiens

<400> SEQUENCE: 8

```
Trp Val Arg Gln Ala Pro Gly Lys Gly Leu Glu Trp Val Ser
1               5                   10
```

<210> SEQ ID NO 9
<211> LENGTH: 29
<212> TYPE: PRT
<213> ORGANISM: Homo sapiens

```
<400> SEQUENCE: 9

Arg Phe Thr Ile Ser Arg Asp Asn Ala Lys Asn Ser Leu Tyr Leu Gln
1               5                   10                  15

Met Asn Ser Leu Arg Ala Glu Asp Met Ala Val Tyr Tyr
            20                  25

<210> SEQ ID NO 10
<211> LENGTH: 11
<212> TYPE: PRT
<213> ORGANISM: Homo sapiens

<400> SEQUENCE: 10

Trp Gly Gln Gly Thr Leu Val Thr Val Ser Ser
1               5                   10

<210> SEQ ID NO 11
<211> LENGTH: 23
<212> TYPE: PRT
<213> ORGANISM: Homo sapiens

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 12
<211> LENGTH: 15
<212> TYPE: PRT
<213> ORGANISM: Homo sapiens

<400> SEQUENCE: 12

Trp Tyr Gln Gln Lys Pro Gly Gln Ala Pro Arg Leu Leu Ile Tyr
1               5                   10                  15

<210> SEQ ID NO 13
<211> LENGTH: 32
<212> TYPE: PRT
<213> ORGANISM: Homo sapiens

<400> SEQUENCE: 13

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 14
<211> LENGTH: 10
<212> TYPE: PRT
<213> ORGANISM: Homo sapiens

<400> SEQUENCE: 14

Phe Gly Gln Gly Thr Lys Leu Glu Ile Lys
1               5                   10

<210> SEQ ID NO 15
<211> LENGTH: 124
<212> TYPE: PRT
<213> ORGANISM: Homo sapiens

<400> SEQUENCE: 15

Glu Val Gln Leu Val Gln Ser Gly Gly Gly Leu Val His Pro Gly Gly
1               5                   10                  15
```

```
Ser Leu Arg Leu Ser Cys Ala Gly Ser Gly Phe Thr Phe Ser Tyr Phe
            20                  25                  30

Ala Met His Trp Val Arg Gln Ala Pro Gly Lys Gly Leu Glu Trp Val
        35                  40                  45

Ser Thr Ile Gly Thr Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Asp Asn Ala Leu Arg Ser Phe Asp Trp Leu Phe Tyr Ser Phe Asp
            100                 105                 110

Tyr Trp Gly Gln Gly Thr Leu Val Thr Val Ser Ser
        115                 120

<210> SEQ ID NO 16
<211> LENGTH: 107
<212> TYPE: PRT
<213> ORGANISM: Homo sapiens

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Tyr Gly Ser Ser Tyr
                85                  90                  95

Thr Phe Gly Gln Gly Thr Lys Leu Glu Ile Lys
            100                 105

<210> SEQ ID NO 17
<211> LENGTH: 454
<212> TYPE: PRT
<213> ORGANISM: Homo sapiens

<400> SEQUENCE: 17

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Tyr Phe
            20                  25                  30

Ala Met His Trp Val Arg Gln Ala Pro Gly Lys Gly Leu Glu Trp Val
        35                  40                  45

Ser Thr Ile Gly Thr Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Asp Asn Ala Leu Arg Ser Phe Asp Trp Leu Phe Tyr Ser Phe Asp
            100                 105                 110
```

Tyr Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 18
<211> LENGTH: 214
<212> TYPE: PRT
<213> ORGANISM: Homo sapiens

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser

-continued

```
                20                  25                  30
Tyr Leu Ala Trp Tyr Gln Gln Lys Pro Gly Gln Ala Pro Arg Leu Leu
            35                  40                  45
Ile Tyr Gly Ala Ser Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Arg Tyr Gly Ser Ser Tyr
                85                  90                  95
Thr Phe Gly Gln Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 19
<211> LENGTH: 5
<212> TYPE: PRT
<213> ORGANISM: Homo sapiens

<400> SEQUENCE: 19

```
Thr Tyr Ala Met His
1               5
```

<210> SEQ ID NO 20
<211> LENGTH: 17
<212> TYPE: PRT
<213> ORGANISM: Homo sapiens

<400> SEQUENCE: 20

```
Val Val Ser Tyr Asp Gly Arg Thr Lys Asp Tyr Ala Asp Ser Val Lys
1               5                   10                  15
Gly
```

<210> SEQ ID NO 21
<211> LENGTH: 10
<212> TYPE: PRT
<213> ORGANISM: Homo sapiens

<400> SEQUENCE: 21

```
Glu Arg Phe Ser Gly Ala Tyr Phe Asp Tyr
1               5                   10
```

<210> SEQ ID NO 22
<211> LENGTH: 11
<212> TYPE: PRT
<213> ORGANISM: Homo sapiens

```
<400> SEQUENCE: 22

Arg Ala Ser Gln Ser Val Ser Ser Tyr Leu Ala
1               5                   10

<210> SEQ ID NO 23
<211> LENGTH: 7
<212> TYPE: PRT
<213> ORGANISM: Homo sapiens

<400> SEQUENCE: 23

Asp Ala Ser Asn Arg Ala Thr
1               5

<210> SEQ ID NO 24
<211> LENGTH: 7
<212> TYPE: PRT
<213> ORGANISM: Homo sapiens

<400> SEQUENCE: 24

Gln Gln Arg Asn Asn Trp Pro
1               5

<210> SEQ ID NO 25
<211> LENGTH: 125
<212> TYPE: PRT
<213> ORGANISM: Homo sapiens

<400> SEQUENCE: 25

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Val Ser Tyr Asp Gly Arg Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Phe Cys
                85                  90                  95

Ala Arg Glu Arg Phe Ser Gly Ala Tyr Phe Asp Tyr Trp Gly Gln Gly
            100                 105                 110

Thr Leu Val Thr Val Ser Ser Ala Ser Thr Lys Gly Pro
        115                 120                 125

<210> SEQ ID NO 26
<211> LENGTH: 107
<212> TYPE: PRT
<213> ORGANISM: Homo sapiens

<400> SEQUENCE: 26

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60
```

Ser Gly Ser Gly Thr Asp Phe Thr Leu Thr Ile Ser Ser Leu Glu Pro
 65                  70                  75                  80

Glu Asp Phe Ala Val Tyr Ser Cys Gln Gln Arg Asn Asn Trp Pro Pro
                 85                  90                  95

Thr Phe Gly Gly Gly Thr Lys Val Glu Ile Lys
                100                 105

<210> SEQ ID NO 27
<211> LENGTH: 1365
<212> TYPE: DNA
<213> ORGANISM: Homo sapiens

<400> SEQUENCE: 27
atggaggttc agctggtgca gtctggggga ggcttggtac atcctggggg gtccctgaga      60
ctctcctgtg caggctctgg attcaccttc agttactttg ctatgcactg ggttcgccag     120
gctccaggaa aagtctgga gtgggtatca actattggta ctggtggtgg cacatactat     180
gcagactccg tgaagggccg attcaccatc tccagagaca atgccaagaa ctccttgtat     240
cttcaaatga acagcctgag agccgaggac atggctgtgt attactgtgc aagagataac     300
gcattacgat cttttgactg gttattttac tcctttgact actggggcca gggaaccctg     360
gtcaccgtct cctcagcttc caccaagggc ccatcggtct tccccctggc accctcctcc     420
aagagcacct ctgggggcac agcggccctg ggctgcctgg tcaaggacta cttccccgaa     480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcaccc agacctacat ctgcaacgtg aatcacaagc ccagcaacac caaggtggac     660
aagagagttg agcccaaatc ttgtgacaaa actcacacat gcccaccgtg cccagcacct     720
gaactcctgg ggggaccgtc agtcttcctc ttccccccaa acccaagga cacctcatg      780 atctcccgga cccctgaggt cacatgcgtg gtggtggacg tgagccacga agaccctgag     840
gtcaagttca actggtacgt ggacggcgtg gaggtgcata atgccaagac aaagccgcgg     900
gaggagcagt acaacagcac gtaccgtgtg gtcagcgtcc tcaccgtcct gcaccaggac     960
tggctgaatg gcaaggagta caagtgcaag gtctccaaca aagccctccc agcccccatc    1020
gagaaaacca tctccaaagc caaagggcag ccccgagaac cacaggtgta caccctgccc    1080
ccatcccggg aggagatgac caagaaccag gtcagcctga cctgcctggt caaaggcttc    1140
tatcccagcg acatcgccgt ggagtgggag agcaatgggc agccggagaa caactacaag    1200
accacgcctc ccgtgctgga ctccgacggc tccttcttcc tctatagcaa gctcaccgtg    1260
gacaagagca ggtggcagca ggggaacgtc ttctcatgct ccgtgatgca tgaggctctg    1320
cacaaccact acacgcagaa gagcctctcc ctgtctccgg gtaaa                   1365

<210> SEQ ID NO 28
<211> LENGTH: 645
<212> TYPE: DNA
<213> ORGANISM: Homo sapiens

<400> SEQUENCE: 28
atggaaattg tgttgacgca gtctccaggc accctgtctt tgtctccagg ggaaagagcc      60
accctctcct gcagggccag tcagagtatt agcagcagct acttagcctg gtaccagcag     120
aaacctggcc aggctcccag gctcctcatc tatggtgcat ccagcagggc cactggcatc     180
ccagacaggt tcagtggcag tgggtctggg acagacttca ctctcaccat cagcagactg     240

```
gagcctgaag attttgcagt gtattactgt cagcggtatg gtagctcata cactttttggc    300 caggggacca agctggagat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagacta cgagaaacac aaagtctacg cctgcgaagt cacccatcag    600
ggcctgagct cgcccgtcac aaagagcttc aacaggggag agtgt                   645
```

HUMAN ANTIBODIES AGAINST RABIES AND USES THEREOF

SEQUENCE LISTING

The instant application contains a Sequence Listing which has been submitted electronically in ASCII format and is hereby incorporated by reference in its entirety. Said ASCII copy, created on Aug. 10, 2016, is named 50720-013WO2_Sequence_Listing_8_10_16_ST25 and is 16,999 bytes in size.

BACKGROUND OF THE INVENTION

Rabies is an acute progressive encephalitis caused by infection with an RNA virus of the family Rhabdoviridae (genus *lyssavirus*). While human rabies fatalities are rare in developed nations (there are usually fewer than 5 deaths in the United States each year), significant numbers of deaths are reported in, for example, India, where 50,000 die of the disease and more than 500,000 are treated. Even in the United States, 15,000 to 40,000 people receive anti-rabies treatment each year. Typically, dogs are the major reservoirs of the disease, but other mammals such as raccoon, skunk, bat, and fox are frequent reservoirs. Transmission of the virus from an animal reservoir to human usually occurs by a bite or scratch that penetrates the skin. Since rabies in humans is almost always fatal, even a suspected infection must be treated with an aggressive post-exposure treatment regimen.

The post-exposure prophylaxis (PEP) of rabies in humans consists of proper wound care, local administration of anti-rabies serum immunoglobulin into and around the wound, and administration of multiple doses of rabies vaccine, usually over several days and weeks. Proper wound care can lessen the amount of virus that survives to enter the patient. Infiltration of the area with anti-rabies serum immunoglobulin can bind to the rabies virus and help clear it, thereby lessening the viral load (by passive immunization). Administration of multiple doses of rabies vaccine (active immunization), usually in the form of a first dose followed by subsequent booster doses, allows for the patient to produce a vigorous active immunity, including humoral and cellular responses. Current sources of anti-rabies serum immunoglobulin are obtained from the blood of vaccinated human donors. Other sources of anti-rabies serum immunoglobulin, for example, murine, are considered not safe for human use. Current sources of rabies vaccines are produced in cell lines and chemically inactivated and lyophilized. While these agents, when administered in time, are highly effective, certain obstacles remain.

For example, human rabies immunoglobulin (HRIG) must be highly purified to prevent the transmission of any adventitious agents because it is harvested from the serum of human donors. In addition, there are few manufacturers of these anti-rabies agents and they remain relatively expensive, especially in the developing world where they are most needed. There is a shortage of HRIG worldwide as a result of the expense involved in producing large quantities of a fractioned blood product. People in developing countries therefore receive "vaccine-only" PEP, which is not recommended by the World Health Organization (WHO). Moreover, the anti-rabies vaccine requires labor intensive cell culture and extensive inactivation and purification steps. Accordingly, improved immunotherapies for treating and preventing rabies infection are needed. Replacement of HRIG with, for example, monoclonal antibodies would provide a cost-effective alternative, resulting in appropriate delivery of PEP to exposed individuals.

SUMMARY OF THE INVENTION

The present invention relates to human antibodies against rabies virus and methods of their use.

In a first aspect, the invention provides an antibody that specifically binds to rabies virus G protein, wherein the antibody comprises a heavy chain variable (VH) domain comprising one, two, or three of the following complementarity determining regions (CDRs): (a) a CDR-H1 comprising the amino acid sequence of GFTFSYFAMH (SEQ ID NO: 1), or a CDR-H1 variant thereof comprising one or more (e.g., one or two) conservative amino acid substitution(s); (b) a CDR-H2 comprising the amino acid sequence of TIGTGGGTYYADSVKG (SEQ ID NO: 2), or a CDR-H2 variant thereof comprising one or more (e.g., one or two) conservative amino acid substitution(s); and/or (c) a CDR-H3 comprising the amino acid sequence of CARDNALRSFDWLFYSFDY (SEQ ID NO: 3), or a CDR-H3 variant thereof comprising one or more (e.g., one or two) conservative amino acid substitution(s). In some embodiments, the VH domain further comprises one, two, three, or four of the following heavy chain variable region framework regions (FRs): (a) an FR-H1 comprising the amino acid sequence of EVQLVQSGGGLVHPGGSLRLSCAGS (SEQ ID NO: 7), or an FR-H1 variant thereof comprising one or more (e.g., one or two) conservative amino acid substitution(s); (b) an FR-H2 comprising the amino acid sequence of WVRQAPGKGLEWVS (SEQ ID NO: 8), or an FR-H2 variant thereof comprising one or more (e.g., one or two) conservative amino acid substitution(s); (c) an FR-H3 comprising the amino acid sequence of RFTISRDNAKNSLYLQMNSLRAEDMAVYY (SEQ ID NO: 9), or an FR-H3 variant thereof comprising one or more (e.g., one or two) conservative amino acid substitution(s); and/or (d) an FR-H4 comprising the amino acid sequence of WGQGTLVTVSS (SEQ ID NO: 10), or an FR-H4 variant thereof comprising one or more (e.g., one or two) conservative amino acid substitution(s). In some embodiments, the VH domain comprises a sequence comprising at least 90% sequence identity (90%, 91%, 92%, 93%, 94%, 95%, 96%, 97%, 98%, or 99% sequence identity) to the amino acid sequence of SEQ ID NO: 15. In some embodiments, the VH domain comprises the amino acid sequence of SEQ ID NO: 15.

In a second aspect, the invention provides an antibody that specifically binds to rabies virus G protein, wherein the antibody comprises a light chain variable (VL) domain comprising one, two, or three of the following CDRs: (a) a CDR-L1 comprising the amino acid sequence of RASQSISSSYLA (SEQ ID NO: 4), or a CDR-L1 variant thereof comprising one or more (e.g., one or two) conservative amino acid substitution(s); (b) a CDR-L2 comprising the amino acid sequence of GASSRAT (SEQ ID NO: 5), or a CDR-L2 variant thereof comprising one or more (e.g., one or two) conservative amino acid substitution(s); and/or (c) a CDR-L3 comprising the amino acid sequence of QRYGSSYT (SEQ ID NO: 6), or a CDR-L3 variant thereof comprising one or more (e.g., one or two) conservative amino acid substitution(s). In some embodiments, the VL domain further comprises one, two, three, or four the following light chain variable region FRs: (a) an FR-L1 comprising the amino acid sequence of EIVLTQSPGTLSLSPGERATLSC (SEQ ID NO: 11), or an FR-L1 variant thereof comprising one or more (e.g., one or two) conservative amino acid substitution(s); (b) an FR-L2 comprising the amino acid sequence of WYQQKPGQAPRLLIY (SEQ ID NO: 12), or an FR-L2 variant thereof comprising one or more (e.g., one or two) conservative amino acid substitution(s); (c) an FR-L3 comprising the amino acid sequence of GIPDRFSGSGSGTDFTLTISRLEPEDFAVYYC (SEQ ID NO: 13), or an FR-L3 variant thereof comprising one or more (e.g., one or two) conservative amino acid substitution(s); and/or (d) an FR-L4 comprising the amino acid sequence of FGQGTKLEIK (SEQ ID NO: 14), or an FR-L4 variant thereof comprising one or more (e.g., one or two) conservative amino acid substitution(s). In some embodiments, the VL domain comprises a sequence comprising at least 90% sequence identity (90%, 91%, 92%, 93%, 94%, 95%, 96%, 97%, 98%, or 99% sequence identity) to the amino acid sequence of SEQ ID NO: 16. In some embodiments, the VL domain comprises the amino acid sequence of SEQ ID NO: 16.

In some embodiments of the first or second aspect, the antibody comprises the following six CDRs: (a) a CDR-H1 comprising the amino acid sequence of GFTFSYFAMH (SEQ ID NO: 1); (b) a CDR-H2 comprising the amino acid sequence of TIGTGGGTYYADSVKG (SEQ ID NO: 2); (c) a CDR-H3 comprising the amino acid sequence of CARDNALRSFDWLFYSFDY (SEQ ID NO: 3); (d) a CDR-L1 comprising the amino acid sequence of RASQSISSSYLA (SEQ ID NO: 4); (e) a CDR-L2 comprising the amino acid sequence of GASSRAT (SEQ ID NO: 5); and (f) a CDR-L3 comprising the amino acid sequence of QRYGSSYT (SEQ ID NO: 6). In some embodiments, the VH domain comprises a sequence comprising at least 90% sequence identity (90%, 91%, 92%, 93%, 94%, 95%, 96%, 97%, 98%, or 99% sequence identity) to the amino acid sequence of SEQ ID NO: 15 and the VL domain comprises a sequence comprising at least 90% sequence identity (90%, 91%, 92%, 93%, 94%, 95%, 96%, 97%, 98%, or 99% sequence identity) to the amino acid sequence of SEQ ID NO: 16. In some embodiments, the VH domain comprises the amino acid sequence of SEQ ID NO: 15 and the VL domain comprises the amino acid sequence of SEQ ID NO: 16.

In a third aspect, the invention features an isolated antibody that competes for binding to rabies virus G protein with the antibody of the first or second aspect.

In a fourth aspect, the invention features an isolated antibody that binds to the same epitope on rabies virus G protein as the antibody of the first or second aspect.

In any of the above aspects, the antibody may be monoclonal, human, humanized, or chimeric. In some embodiments, the antibody is an antibody fragment that binds rabies virus G protein. For example, in some embodiments, the antibody fragment is selected from the group consisting of Fab, Fab'-SH, Fv, scFv, and (Fab')$_2$ fragments. In other embodiments, the antibody is a full-length antibody. In some embodiments, the full-length antibody comprises (a) a heavy chain sequence comprising at least 90% sequence identity (90%, 91%, 92%, 93%, 94%, 95%, 96%, 97%, 98%, or 99% sequence identity) to the amino acid sequence of SEQ ID NO: 17; (b) a light chain sequence comprising at least 90% sequence identity (90%, 91%, 92%, 93%, 94%, 95%, 96%, 97%, 98%, or 99% sequence identity) to the amino acid sequence of SEQ ID NO: 18; or (c) a heavy chain sequence as in (a) and a light chain sequence as in (b). In some embodiments, the full-length antibody comprises (a) a heavy chain sequence comprising the amino acid sequence of SEQ ID NO: 17; (b) a light chain sequence comprising the amino acid sequence of SEQ ID NO: 18; or (c) a heavy chain sequence as in (a) and a light chain sequence as in (b).

In some embodiments, the antibody is an IgG antibody. For example, in some embodiments, the antibody (e.g., the full-length antibody) is an IgG1 antibody. In other embodiments, the antibody (e.g., the full-length antibody) is an IgG3 antibody.

In some embodiments, the antibody binds to an epitope in antigenic site II of rabies virus G protein. In some embodiments, the epitope comprises amino acid residue Glu33. In some embodiments, the epitope comprises amino acid residue Cys35. In some embodiments, the epitope comprises amino acid residue Glu33 and Cys35. In some embodiments, the antibody is capable of neutralizing a rabies virus comprising a mutation in antigenic site III of rabies virus G protein. In some embodiments, the antibody is capable of neutralizing a rabies virus comprising a mutation at amino acid residue I338 in antigenic site III of rabies virus G protein. In some embodiments, the antibody is capable of neutralizing a rabies virus comprising an I338T mutation in antigenic site III of rabies virus G protein, such as the bat rabies virus variant "3860 bat."

In any of the above aspects, the antibody may bind to rabies virus G protein with a $K_D$ of about 1 μM or lower. In some embodiments, the antibody may bind to rabies virus G protein with a $K_D$ of about 500 nM or lower. In some embodiments, the antibody may bind to rabies virus G protein with a $K_D$ of about 250 nM or lower. In some embodiments, the antibody may bind to rabies virus G protein with a $K_D$ of about 125 nM or lower. In some embodiments, the antibody may bind to rabies virus G protein with a $K_D$ of about 100 nM or lower. In some embodiments, the antibody may bind to rabies virus G protein with a $K_D$ of about 50 nM or lower. In some embodiments, the antibody may bind to rabies virus G protein with a $K_D$ of about 1 nM or lower. In some embodiments, the antibody may bind to rabies virus G protein with a $K_D$ between about 1 nM and about 500 nM. In some embodiments, the antibody may bind to rabies virus G protein with a $K_D$ between about 50 nM and about 500 nM. In some embodiments, the antibody may bind to rabies virus G protein with a $K_D$ between about 50 nM and about 250 nM. In some embodiments, the antibody may bind to rabies virus G protein with a $K_D$ between about 100 nM and about 250 nM. In some embodiments, the antibody may bind to rabies virus G protein with a $K_D$ between about 100 nM and about 200 nM. In some embodiments, the antibody may bind to rabies virus G protein with a $K_D$ between about 100 nM and about 150 nM. In some embodiments, the antibody may bind to rabies virus G protein with a $K_D$ of about 125 nM. In any of these embodiments, the $K_D$ may be measured by any art-recognized method, such as surface plasmon resonance (SPR) (e.g., BIACORE®).

In a fifth aspect, the invention provides a pharmaceutical composition comprising the antibody of any one of the above aspects. In some embodiments, the pharmaceutical composition further comprises a second antibody that binds to a different epitope of rabies virus G protein. For example, in some embodiments, the second antibody comprises the following six CDRs: (a) a CDR-H1 comprising the amino acid sequence of TYAMH (SEQ ID NO: 19); (b) a CDR-H2 comprising the amino acid sequence of VVSYDGRTKDYADSVKG (SEQ ID NO: 20); (c) a CDR-H3 comprising the amino acid sequence of ERFSGAYFDY (SEQ ID NO: 21); (d) a CDR-L1 comprising the amino acid sequence of RASQSVSSYLA (SEQ ID NO: 22); (e) a CDR-L2 comprising the amino acid sequence of DASNRAT (SEQ ID NO: 23); and (f) a CDR-L3 comprising the amino acid sequence of QQRNNWP (SEQ ID NO: 24). In some embodiments, the second antibody comprises (a) a VH domain comprising a sequence having at least 90% sequence identity (90%, 91%, 92%, 93%, 94%, 95%, 96%, 97%, 98%, or 99% sequence identity) to the amino acid sequence of SEQ ID NO: 25 or (b) a VL domain comprising a sequence having at least 90% sequence identity (90%, 91%, 92%, 93%, 94%, 95%, 96%, 97%, 98%, or 99% sequence identity) to the amino acid sequence of SEQ ID NO: 26. In some embodiments, the second antibody comprises (a) a VH domain comprising a sequence having at least 90% sequence identity (90%, 91%, 92%, 93%, 94%, 95%, 96%, 97%, 98%, or 99% sequence identity) to the amino acid sequence of SEQ ID NO: 25 and (b) a VL domain comprising a sequence having at least 90% sequence identity (90%, 91%, 92%, 93%, 94%, 95%, 96%, 97%, 98%, or 99% sequence identity) to the amino acid sequence of SEQ ID NO: 26. In some embodiments, the second antibody comprises (a) a VH domain comprising the amino acid sequence of SEQ ID NO: 25 or (b) a VL domain comprising the amino acid sequence of SEQ ID NO: 26.

In some embodiments, the second antibody comprises (a) a VH domain comprising the amino acid sequence of SEQ ID NO: 25 and (b) a VL domain comprising the amino acid sequence of SEQ ID NO: 26. In other embodiments, the pharmaceutical composition comprising the antibody of any one of the above aspects further comprises HRIG. In some embodiments, the pharmaceutical composition further comprises a pharmaceutically acceptable carrier, excipient, or diluent. In some embodiments, the pharmaceutical composition is formulated for treating a subject having a rabies virus infection. In some embodiments, the pharmaceutical composition is formulated for treating a subject at risk of developing a rabies virus infection. In some embodiments, the subject is a human.

In a sixth aspect, the invention features a nucleic acid (e.g., an isolated nucleic acid molecule) encoding one or more antibodies (e.g., 1, 2, or 3 or more antibodies) of the first, second, third, and/or fourth aspects.

In a seventh aspect, the invention features a vector (e.g., AAV, plasmids, lentiviral vectors, etc.) comprising a nucleic acid of the sixth aspect.

In an eighth aspect, the invention features a host cell comprising a vector of the seventh aspect. In some embodiments, the host cell is a mammalian cell (e.g., a Chinese hamster ovary (CHO) cell). In other embodiments, the host cell is a prokaryotic cell (e.g., *E. coli*).

In a ninth aspect, the invention features a method of producing an antibody of the first, second, third, and/or fourth aspect, the method comprising culturing a host cell of the eighth aspect in a culture medium. In some embodiments, the method further comprises recovering the antibody from the host cell or the culture medium.

In a tenth aspect, the invention provides a method of treating a subject having a rabies virus infection comprising administering to the subject a therapeutically effective amount of the antibody of any the first, second, third, and/or fourth aspect or the pharmaceutical composition of the fifth aspect, thereby treating the subject.

In an eleventh aspect, the invention provides a method of treating a subject at risk of developing a rabies virus infection comprising administering to the subject a therapeutically effective amount of the antibody of the first, second, third, and/or fourth aspect or the pharmaceutical composition of the fifth aspect, thereby treating the subject.

In certain embodiments of the tenth or eleventh aspect, the antibody is administered to the subject in a dosage of about 0.001 mg/kg to about 50 mg/kg (e.g., about 0.01 mg/kg to about 50 mg/kg, e.g., about 0.1 mg/kg to about 50 mg/kg, e.g., about 1 mg/kg to about 50 mg/kg, e.g., about 10 mg/kg to about 50 mg/kg, e.g., about 22 mg/kg). In certain embodiments, the antibody is administered to the subject in a dosage of about 0.001 IU/kg to about 50 IU/kg (e.g., about 0.01 IU/kg to about 50 IU/kg, e.g., about 0.1 IU/kg to about 50 IU/kg, e.g., about 1 IU/kg to about 50 IU/kg, e.g., about 10 IU/kg to about 50 IU/kg, e.g., about 20 IU/kg). In some embodiments, the antibody or pharmaceutical composition is administered intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions.

In some embodiments, the subject is administered at least one dose of the antibody or the pharmaceutical composition. In some embodiments, the subject is administered at least two doses of the antibody or the pharmaceutical composition. In some embodiments, the subject is administered at least three doses of the antibody or the pharmaceutical composition. In some embodiments, the subject is administered at least four doses of the antibody or the pharmaceutical composition. In some embodiments, the subject is administered at least five doses of the antibody or the pharmaceutical composition. In some embodiments, the subject is administered at least one dose of the antibody or the pharmaceutical composition and subsequently administered at least one (e.g., at least one, two three, four, or five doses of HRIG or a pharmaceutical composition thereof. In some embodiments, the subject is a human.

Other features and advantages of the invention will be apparent from the following description of the preferred embodiments thereof, and from the claims.

BRIEF DESCRIPTION OF THE DRAWINGS

Figures 1, 2:
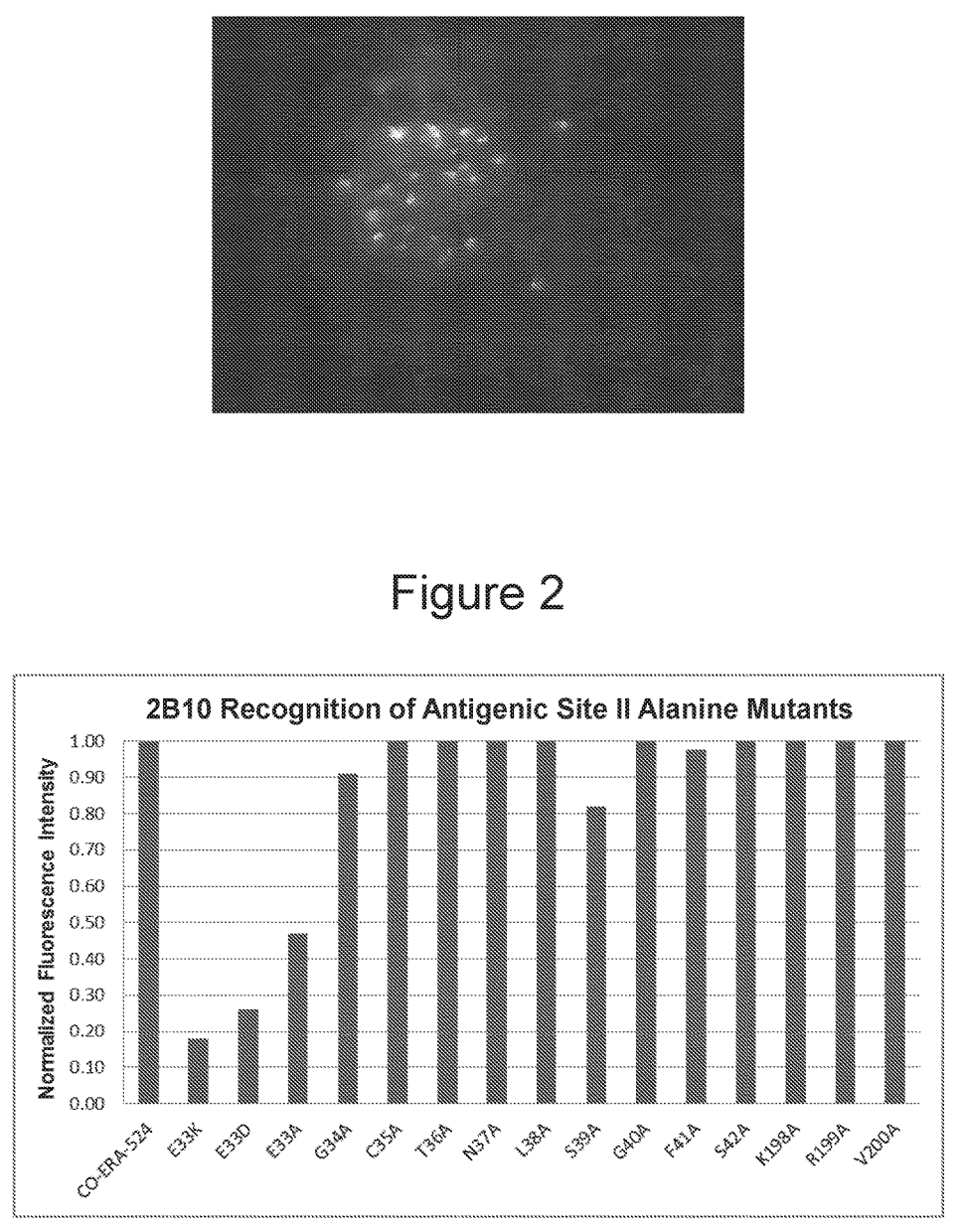

FIG. 1 is a fluorescence image of a Rapid Fluorescent Focus Inhibition Test (RIFFIT) assay showing that rabies virus having an E33K substitution mutation in its G glycoprotein conferred resistance and escape from neutralization of the anti-rabies virus HuMab 2B10.

FIG. 2 is a graph showing the fluorescence intensity, as analyzed by flow cytometry, of the indicated antigenic site II G glycoprotein alanine-scanning mutants following incubation with the 2B10 antibody and detection by a fluorescently labeled secondary antibody. The individual fluorescence intensity was normalized against the binding signal of the 17C7 antibody, used as an internal control for G glycoprotein expression. The results of the alanine scanning mutagenesis study indicate that residue 33 of the G glycoprotein is a critical epitopic residue for 2B10 binding.

DETAILED DESCRIPTION OF EMBODIMENTS OF THE INVENTION

I. Definitions

Figure 3:
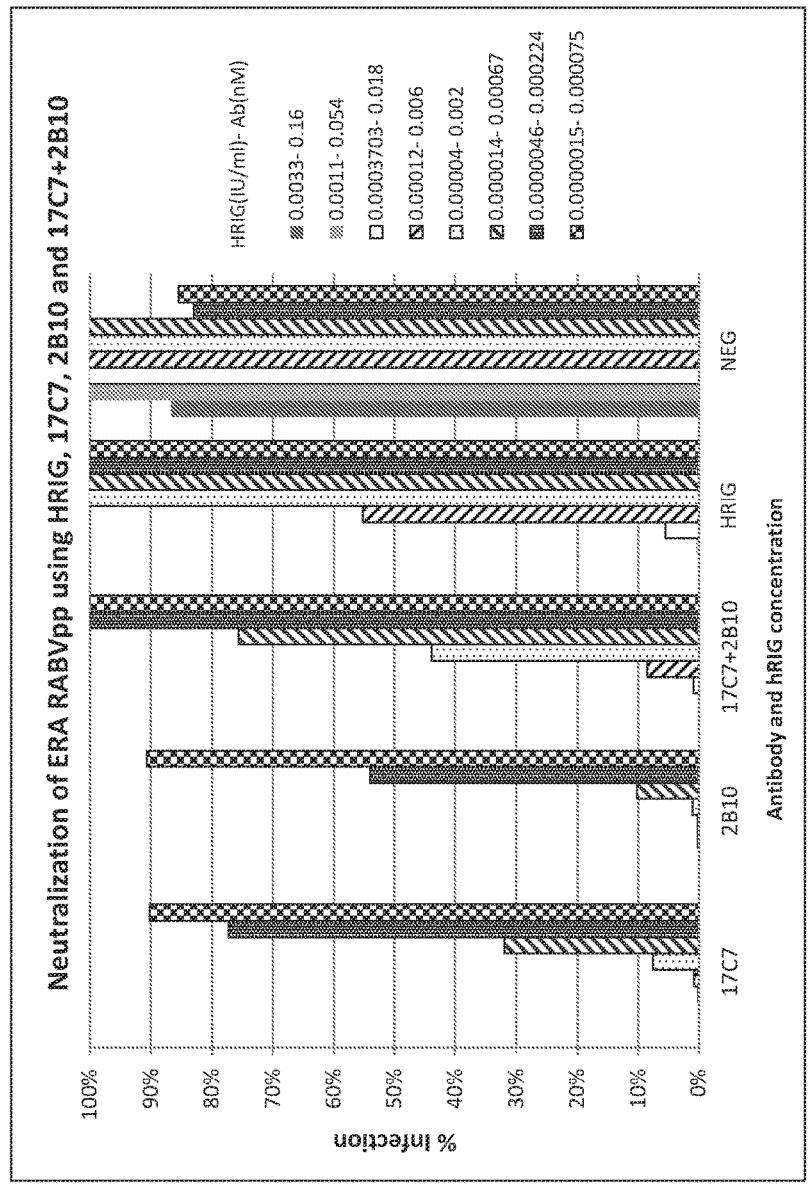
FIG. 3 is a graph of the results of an in vitro rabies pseudovirus infection/neutralization assay, showing that 2B10, 17C7, and a combination of 2B10 and 17C7 are all capable of neutralizing rabies pseudotyped viral particles (RABVpp) expressing G glycoprotein of the ERA strain of rabies virus.
Figure 4:
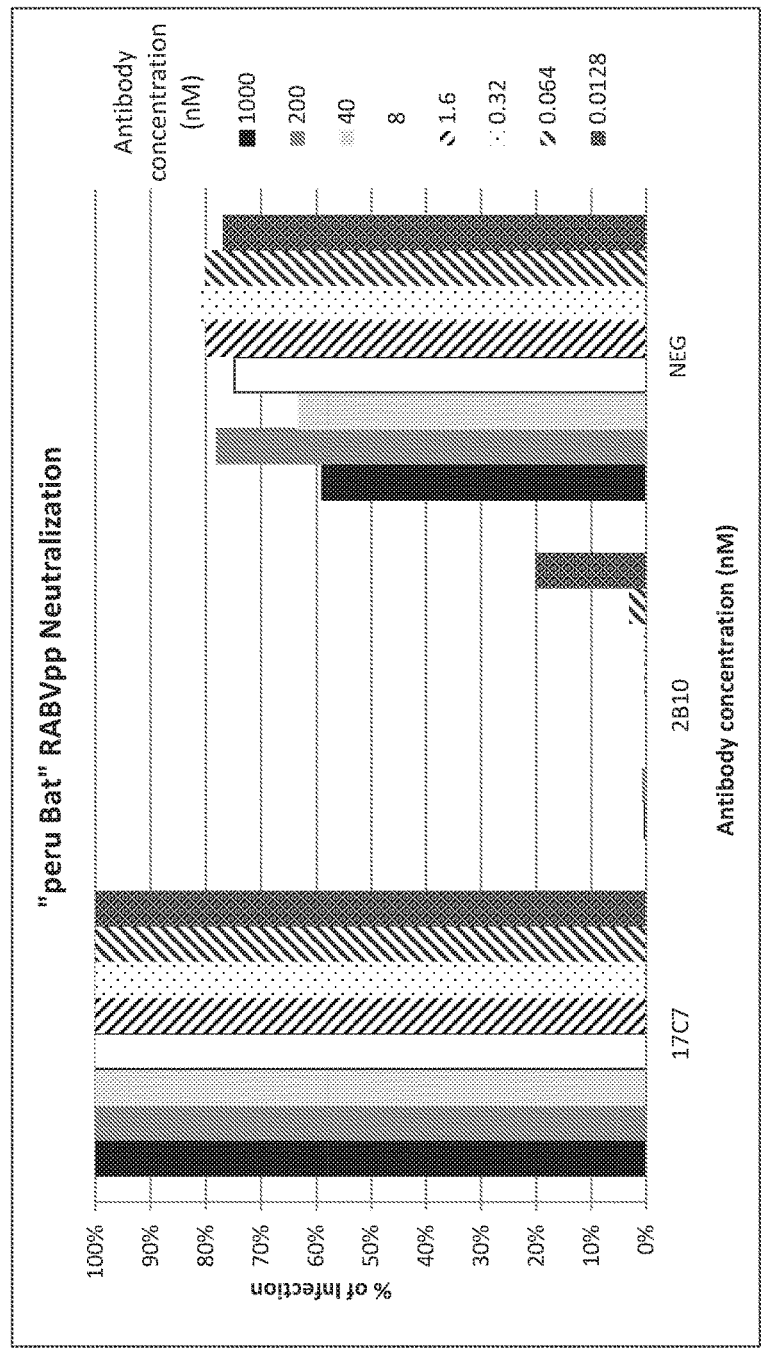
FIG. 4 is a graph of the results of an in vitro rabies pseudovirus infection/neutralization assay, showing that 2B10, but not 17C7, is capable of neutralizing RABVpp expressing G glycoprotein of the "Peru bat" street isolate of rabies virus.
Figure 5:
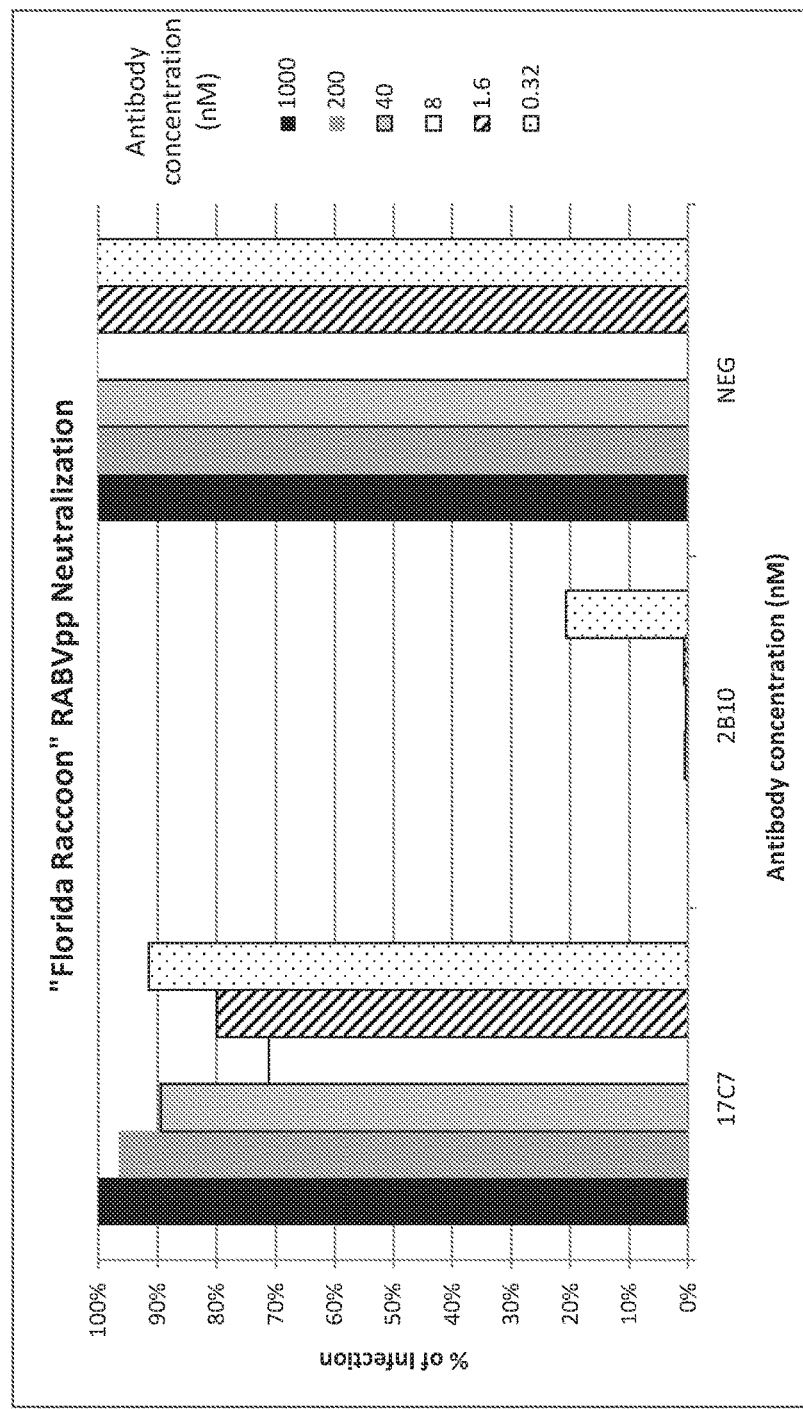
FIG. 5 is a graph of the results of an in vitro rabies pseudovirus infection/neutralization assay, showing that 2B10, but not 17C7, is capable of neutralizing RABVpp expressing G glycoprotein of the "Florida raccoon" street isolate of rabies virus.
Figure 6A:
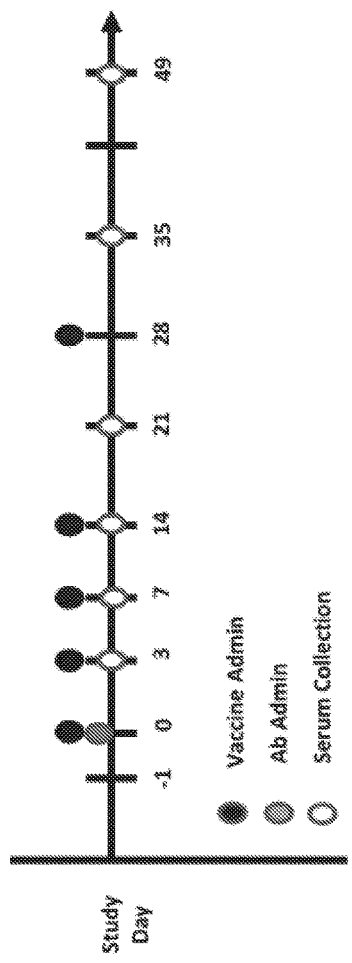
FIG. 6A shows the experimental design of the vaccine interference study, with a schematic diagram showing a timeline for vaccine and antibody treatments (top) and a table showing test group and dosing information.
Figure 6B:
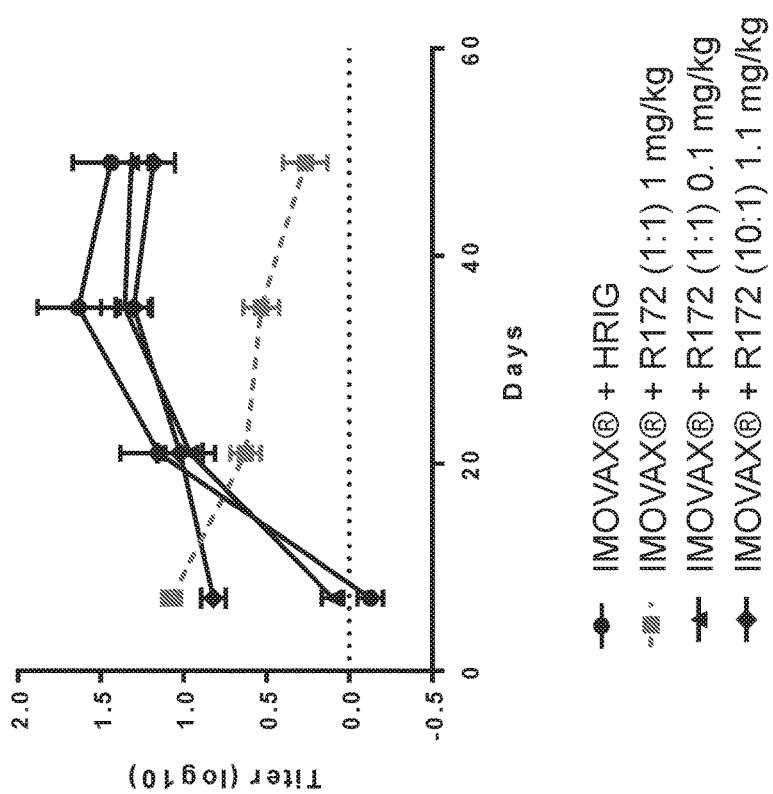
FIG. 6B is a graph showing the average RFFIT titer determined for each test group in the vaccine interference study.

As used herein, the term "rabies virus" refers to the virion or portion thereof (e.g., protein portion thereof, such as a rabies virus G glycoprotein) that is encoded by the RNA of rabies virus.

The term "anti-rabies virus antibody" is an antibody that interacts with (e.g., binds to) a rabies virus or a protein, carbohydrate, lipid, or other component produced by or associated with rabies virus.

The term "rabies virus G glycoprotein antibody" or "an antibody that specifically binds to rabies virus G protein" refers to an antibody that is capable of binding a G glycoprotein of rabies virus or a fragment thereof with sufficient affinity such that the antibody is useful as a preventative, diagnostic, and/or therapeutic agent in targeting a G glycoprotein of rabies virus. An anti-rabies virus or G glycoprotein antibody may bind to an epitope, e.g., a conformational or a linear epitope, or to a portion or fragment of the virus or component thereof, such as all or a portion of the antigenic site II of the G glycoprotein of rabies virus. In certain embodiments, the epitope comprises amino acid residue Glu33 of the G glycoprotein of rabies virus. In certain embodiments, the epitope comprises Glu33 and/or Cys35 of the G glycoprotein of rabies virus. In certain embodiments, an antibody that binds to the G glycoprotein of rabies virus has a dissociation constant ($K_D$) of $\leq 1$ µM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g. from $10^{-8}$ M to $10^{-13}$ M, e.g., from $10^{-9}$ M to $10^{-13}$ M).

An "antibody" is a protein including at least one or two, heavy (H) chain variable regions (abbreviated herein as VH), and at least one or two light (L) chain variable regions (abbreviated herein as VL). The VH and VL regions can be further subdivided into regions of hypervariability, termed "complementarity determining regions" (CDRs), interspersed with regions that are more conserved, termed "framework regions" (FR). The extent of the framework region and CDRs has been precisely defined (see, Kabat, E. A. et al., *Sequences of Proteins of Immunological Interest*, Fifth Edition, U.S. Department of Health and Human Services, NIH Publication No. 91-3242, 1991, and Chothia, C. et al., *J. Mol. Biol.* 196:901-917, 1987, which are incorporated herein by reference). Preferably, each VH and VL is composed of three CDRs and four FRs, arranged from amino-terminus to carboxy-terminus in the following order: FRI, CDRI, FR2, CDR2, FR3, CDR3, FR4.

The VH or VL regions of the antibody can further include all or part of a heavy or light chain constant region. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CHI, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

The term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta (IgD), epsilon (IgE), and mu (IgM) constant region genes, as well as the myriad immunoglobulin variable region genes. Full-length immunoglobulin "light chains" (about 25 $K_D$ and 214 amino acids) are encoded by a variable region gene at the $NH_2$-terminus (about 110 amino acids) and a kappa or lambda constant region gene at the COOH-terminus. Full-length immunoglobulin "heavy chains" (about 50 $K_D$ and 446 amino acids), are similarly encoded by a variable region gene (about 116 amino acids) and one of the other aforementioned constant region genes, e.g., gamma (encoding about 330 amino acids). The term "immunoglobulin" includes an immunoglobulin having: CDRs from a human or non-human source. The framework of the immunoglobulin can be human, humanized, or non-human, e.g., a murine framework modified to decrease antigenicity in humans, or a synthetic framework, e.g., a consensus sequence. A mature immunoglobulin/antibody variable region is typically devoid of a leader sequence. Immunoglobulins/antibodies can be further distinguished by their constant regions into class (e.g., IgA, IgD, IgE, IgG, or IgM) and subclass or isotype (e.g., IgG1, IgG2, IgG3, or IgG4).

The terms "full-length antibody," "intact antibody," and "whole antibody" are used herein interchangeably to refer to an antibody having a structure substantially similar to a native antibody structure or having heavy chains that contain an Fc region as defined herein.

The term "human antibody" is an antibody that has variable and constant regions derived from human germline immunoglobulin sequences. The human antibodies described herein may include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences (i.e., humanized antibodies).

An anti-rabies virus antibody, or antigen-binding portion thereof, can be administered alone or in combination with a second agent. The subject can be a patient infected or suspected to be infected with rabies virus or having a symptom of rabies virus-mediated disease (e.g., a neuropathology, encephalomyelitis, or anti-rabies immunoglobulin serum titer). The treatment can be used to cure, heal, alleviate, relieve, alter, remedy, ameliorate, palliate, improve, or affect the infection and the disease associated with the infection, the symptoms of the disease, or a predisposition toward the disease. For the clinical management of rabies virus infection, "treatment" is frequently understood to mean the prophylaxis or prevention of a productive infection before the onset of illness.

An amount of an anti-rabies virus antibody effective to treat a rabies virus infection, or a "therapeutically effective amount" is an amount of the antibody that is effective, upon single or multiple dose administration to a subject, in inhibiting rabies virus infection, disease, or sequelae thereof, in a subject. A therapeutically effective amount of the antibody or antibody fragment may vary according to factors such as the disease state, wound site, rabies virus strain or isolate, animal vector of rabies virus, age, sex, and weight of the individual, and the ability of the antibody or antibody portion to elicit a desired response in the individual. A therapeutically effective amount is also one in which any toxic or detrimental effects of the antibody or antibody portion is outweighed by the therapeutically beneficial effects. The ability of an antibody to inhibit a measurable parameter can be evaluated in an animal model system predictive of efficacy in humans. For example, the ability of an anti-rabies virus antibody to protect hamsters from lethal challenge with rabies virus can predict efficacy in humans, as described in the Examples. Alternatively, this property of an antibody or antibody composition can be evaluated by examining the ability of the compound to modulate rabies virus/cell interactions, e.g., binding, infection, virulence, and the like, by in vitro by assays known to the skilled practitioner. In vitro assays include binding assays, such as ELISA, and neutralization assays.

An amount of an anti-rabies virus antibody effective to prevent a disorder or disease, or a "prophylactically effective amount," of the antibody is an amount that is effective, upon single-dose or multiple-dose administration to the subject, in preventing or delaying the occurrence of the onset or recurrence of rabies virus, or inhibiting a symptom thereof. However, if longer time intervals of protection are desired, increased doses or more frequent doses can be administered.

The terms "antagonize", "induce", "inhibit", "potentiate", "elevate", "increase", "decrease", or the like, e.g., which denote quantitative differences between two states, refer to a difference, e.g., a statistically or clinically significant difference, between the two states.

The term "specific binding" or "specifically binds to" refers to the ability of an antibody to bind to a rabies virus, or portion thereof, with an affinity of at least $1 \times 10^{-6}$ M, and/or bind to a rabies virus, or portion thereof, with an affinity that is at least two-fold greater than its affinity for a non-specific antigen.

The term "antigen-binding portion" or "antigen-binding fragment" of an antibody (or simply "antibody portion," "portion," or "fragment"), as used herein, refers to a portion/fragment of an antibody that specifically binds to a rabies virus or component thereof (e.g., rabies virus G glycoprotein), e.g., a molecule in which one or more immunoglobulin chains is not full length, but which specifically binds to a rabies virus or component thereof. Examples of binding portions/fragments encompassed within the term include an "antibody fragment," which refers to a molecule other than an intact antibody that comprises a portion of an intact antibody that specifically binds to the antigen (e.g., rabies virus G glycoprotein) to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. These antibody fragments are obtained using conventional techniques, and the fragments are screened for utility in the same manner as are intact antibodies. Antibody fragments can be produced by recombinant DNA techniques, or by enzymatic or chemical cleavage of intact immunoglobulins.

The term "monoclonal antibody," as used herein, refers to an antibody which displays a single binding specificity and affinity for a particular epitope. Accordingly, the term "human monoclonal antibody," or "HuMab," refers to an antibody which displays a single binding specificity and which has variable and constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "about" as used herein refers to the usual error range for the respective value readily known to the skilled person in this technical field. Reference to "about" a value or parameter herein includes (and describes) embodiments that are directed to that value or parameter per se.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described below.

The term "$K_D$," as used herein, is intended to refer to the dissociation equilibrium constant of a particular antibody-antigen interaction. Typically, the antibodies of the invention bind to rabies virus G protein with a dissociation equilibrium constant ($K_D$) of less than about $10^{-6}$ M, such as less than approximately $10^{-7}$ M, $10^{-8}$ M, $10^{-9}$ M, or $10^{-10}$ M or even lower when determined by surface plasmon resonance (SPR) technology or other conventional means.

A "disease" is any condition that would benefit from treatment including, but not limited to, chronic and acute disorders or diseases including those pathological conditions which predispose the mammal to the disease in question.

As used herein, the term "rabies virus infection" refers to any infection or disease, the onset, progression, or the persistence of the symptoms of which requires the participation of a rabies virus.

The term "EC50," as used herein, refers to the concentration of an antibody or an antigen-binding portion thereof, which induces a response, either in an in vivo or an in vitro assay, such as a neutralization assay described herein, which is 50% of the maximal response (i.e., halfway between the maximal response and the baseline).

The term "epitope" or "antigenic determinant" refers to a site on an antigen to which an immunoglobulin or antibody specifically binds (e.g., antigenic site II of the G glycoprotein of rabies virus, e.g., an epitope including amino acid residue(s) Glu33 and/or Cys35 of the G glycoprotein of rabies virus).

Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 2, 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance. See, for example, Epitope Mapping Protocols in Methods in Molecular Biology, Vol. 66, G. E. Morris, Ed. (1996). Epitopes can also be defined by point mutations in the target protein (e.g., G glycoprotein of rabies virus), which affect the binding of the antibody (e.g., monoclonal antibody).

The term "host cell," as used herein, is intended to refer to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

An "isolated antibody" is one which has been identified and separated and/or recovered from a component of its natural environment and/or is substantially free of other antibodies having different antigenic specificities (e.g., an isolated antibody that specifically binds to the G glycoprotein of rabies virus is substantially free of antibodies that specifically bind antigens other than the G glycoprotein of rabies virus). Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie™ blue or, preferably, silver stain. Isolated antibody includes the antibody in situ within recombinant cells since at least one component of the antibody's natural environment will not be present. Similarly, isolated antibody includes the antibody in medium around recombinant cells. Ordinarily, however, isolated antibody will be prepared by at least one purification step.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid," as used herein in reference to nucleic acids molecules encoding antibodies or antibody portions (e.g., VH, VL, CDRs) that bind to the G glycoprotein of rabies virus, is intended to refer to a nucleic acid molecule in which the nucleotide sequences encoding the antibody or antibody portion are free of other nucleotide sequences encoding antibodies that bind antigens other than the G glycoprotein of rabies virus, which other sequences may naturally flank the nucleic acid in human genomic DNA.

The term "recombinant" antibody, as used herein, refers to antibodies that are prepared, expressed, created, or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created, or isolated by any other means that involves splicing of human immunoglobulin gene sequences to other DNA sequences. Such recombinant antibodies include humanized, CDR grafted, chimeric, in vitro generated (e.g., by phage display) antibodies, and may optionally include constant regions derived from human germline immunoglobulin sequences.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "substantially identical" (or "substantially homologous") refers to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the first antibody.

Calculations of "homology" between two sequences are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 50% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences can be accomplished using a mathematical algorithm. The percent homology between two amino acid sequences is determined using the Needleman and Wunsch, *J. Mol. Biol.* 48:444-453, 1970, algorithm which has been incorporated into the GAP program in the GCG software package, using a Blossum 62 scoring matrix with a gap penalty of 12, a gap extend penalty of 4, and a frame shift gap penalty of 5.

It is understood that the antibodies and antigen-binding portions thereof described herein may have additional conservative or non-essential amino acid substitutions, which do not have a substantial effect on the polypeptide functions. Whether or not a particular substitution will be tolerated, i.e., will not adversely affect desired biological properties, such as binding activity, can be determined as described in Bowie et al., *Science*, 247:1306-1310,1990. A "conservative amino acid substitution" is one in which an amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of a polypeptide, such as a binding agent, e.g., an antibody, without substantially altering a biological activity, whereas an "essential" amino acid residue results in such a change.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

A "subject" or an "individual" is a mammal. Mammals include, but are not limited to, domesticated animals (e.g., cows, sheep, cats, dogs, and horses), primates (e.g., humans and non-human primates such as monkeys), rabbits, deer, and rodents (e.g., mice and rats). In certain embodiments, the subject or individual is a human.

The terms "treat," "treating," and "treatment," as used herein, refer to preventative or therapeutic measures described herein. The methods of "treatment" employ administration to a subject in need of such treatment an antibody of the present invention, for example, a subject at risk of developing a rabies virus infection or a subject having a rabies virus infection, in order to prevent, cure, delay, reduce the severity of, or ameliorate one or more symptoms of the disorder or recurring disorder, or in order to prolong the survival of a subject beyond that expected in the absence of such treatment. In some embodiments, for example, the anti-rabies virus antibodies of the invention would be administered to a subject at risk of developing a disorder associated with a rabies virus infection (e.g., a subject residing or traveling to a geographical location in which rabies virus-related infections and/or fatalities is prevalent, e.g., India). Desirable effects of treatment include, but are not limited to, preventing occurrence of disease or disorder, such as a disorder associated with a rabies virus infection. Other desirable effects of treatment may include preventing recurrence of disease, alleviation of symptoms, diminishment of any direct or indirect pathological consequences of the disease, decreasing the rate of disease progression, amelioration or palliation of the disease state, and improved prognosis.

As used herein, "administering" is meant a method of giving a dosage of a compound (e.g., an anti-rabies virus antibody of the invention or a nucleic acid encoding an anti-rabies virus antibody of the invention) or a composition (e.g., a pharmaceutical composition, e.g., a pharmaceutical composition including an anti-rabies virus antibody of the invention) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. The method of administration can vary depending on various factors (e.g., the compound or composition being administered and the severity of the condition, disease, or disorder being treated).

II. Compositions and Methods

In one aspect, the invention is based, in part, on anti-rabies virus antibodies. Antibodies of the invention are useful, for example, for treating a subject having, or at risk of developing, a rabies virus disorder.

A. Anti-Rabies Virus Antibodies

The invention provides isolated antibodies that bind to the G glycoprotein of rabies virus.

In one aspect, the invention provides an antibody that specifically binds to rabies virus G protein, wherein the antibody comprises a heavy chain variable (VH) domain comprising one or more (e.g., 1, 2, or 3) of the following complementarity determining regions (CDRs): (a) a CDR-H1 comprising the amino acid sequence of GFTFSYFAMH (SEQ ID NO: 1); (b) a CDR-H2 comprising the amino acid sequence of TIGTGGGTYYADSVKG (SEQ ID NO: 2); and (c) a CDR-H3 comprising the amino acid sequence of CARDNALRSFDWLFYSFDY (SEQ ID NO: 3), or one or more (e.g., 1, 2, or 3) variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to SEQ ID NOs: 1-3.

In some instances, the VH domain of the antibody further comprises one or more (e.g., 1, 2, 3, or 4) of the following heavy chain variable region framework regions (FRs): (a) an FR-H1 comprising the amino acid sequence of EVQLVQSGGGLVHPGGSLRLSCAGS (SEQ ID NO: 7); (b) an FR-H2 comprising the amino acid sequence of WVRQAPGKGLEWVS (SEQ ID NO: 8); (c) an FR-H3 comprising the amino acid sequence of RFTISADTSKNTAYLQMNSLRAEDTAVYY (SEQ ID NO: 9); and (d) an FR-H4 comprising the amino acid sequence of WGQGTLVTVSS (SEQ ID NO: 10), or one or more (e.g., 1, 2, 3, or 4) variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to SEQ ID NOs: 8-10. In some instances, the VH domain comprises a sequence comprising at least 90% sequence identity (e.g., 91%, 92%, 93%, 94%, 95%, 96%, 97%, 98%, or 99% identity) to, or the sequence of, the amino acid sequence of SEQ ID NO: 15.

In another aspect of the invention, the invention provides an antibody that specifically binds to rabies virus G protein, wherein the antibody comprises a light chain variable (VL) domain comprising one or more (e.g., 1, 2, or 3) of the following CDRs: (a) a CDR-L1 comprising the amino acid sequence of RASQSISSSYLA (SEQ ID NO: 4); (b) a CDR-L2 comprising the amino acid sequence of GASSRAT (SEQ ID NO: 5); and (c) a CDR-L3 comprising the amino acid sequence of QRYGSSYT (SEQ ID NO: 6), or one or more (e.g., 1, 2, or 3) variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to SEQ ID NOs: 4-6.

In some instances, the VL domain further comprises one or more (e.g., 1, 2, 3, or 4) of the following light chain variable region FRs: (a) an FR-L1 comprising the amino acid sequence of EIVLTQSPGTLSLSPGERATLSC (SEQ ID NO: 11); (b) an FR-L2 comprising the amino acid sequence of WYQQKPGQAPRLLIY (SEQ ID NO: 12); (c) an FR-L3 comprising the amino acid sequence of GIPDRFSGSGSGTDFTLTISRLEPEDFAVYYC (SEQ ID NO: 13); and (d) an FR-L4 comprising the amino acid sequence of FGQGTKLEIK (SEQ ID NO: 14), or one or more (e.g., 1, 2, 3, or 4) variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to SEQ ID NOs: 11-14. In some instances, the VH domain comprises a sequence comprising at least 90% sequence identity (e.g., 91%, 92%, 93%, 94%, 95%, 96%, 97%, 98%, or 99% identity) to, or the sequence of, the amino acid sequence of SEQ ID NO: 16.

In some instances, for example, the antibody may include the following six CDRs: (a) a CDR-H1 comprising the amino acid sequence of GFTFSYFAMH (SEQ ID NO: 1); (b) a CDR-H2 comprising the amino acid sequence of TIGTGGGTYYADSVKG (SEQ ID NO: 2); (c) a CDR-H3 comprising the amino acid sequence of CARDNALRSFDWLFYSFDY (SEQ ID NO: 3); (d) a CDR-L1 comprising the amino acid sequence of RASQSISSSYLA (SEQ ID NO: 4); (e) a CDR-L2 comprising the amino acid sequence of GASSRAT (SEQ ID NO: 5); and (f) a CDR-L3 comprising the amino acid sequence of QRYGSSYT (SEQ ID NO: 6), or a combination of one or more of the above CDRs and one or more variants thereof having at least 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-6. In some instances, the antibody comprises (a) a VH sequence having at least 90% sequence identity (e.g., at least 91%, 92%, 93%, 94%, 95%, 96%, 97%, 98%, or 99% sequence identity) to, or the sequence of, SEQ ID NO: 15, and (b) a VL sequence having at least 90% sequence identity (e.g., at least 91%, 92%, 93%, 94%, 95%, 96%, 97%, 98%, or 99% sequence identity) to, or the sequence of, SEQ ID NO: 16.

In another aspect, the invention provides isolated antibodies that compete for binding to rabies virus G protein with an anti-rabies virus antibody described above, such as an antibody having the six CDR sequences of SEQ ID NOs: 1-6. In another aspect, the invention provides isolated antibodies that bind to the same epitope on rabies virus G protein as an anti-rabies virus antibody described above, such as an antibody having the six CDR sequences of SEQ ID NOs: 1-6.

In some instances, an anti-rabies virus antibody described above may bind to an epitope in antigenic site II of rabies virus G protein. The epitope may comprise amino acid residue Glu33 of rabies virus G protein, amino acid residue Cys35 of rabies virus G protein, or both. In some instances, the antibody is capable of neutralizing a rabies virus comprising a mutation in antigenic site III of rabies virus G protein. In some instances, the antibody is capable of neutralizing a rabies virus comprising a mutation at amino acid residue I338 in antigenic site III of rabies virus G protein. In some instances, the antibody is capable of neutralizing a rabies virus comprising an I338T mutation in antigenic site III of rabies virus G protein, such as the bat rabies virus variant "3860 bat."

In some instances, the anti-rabies virus antibodies described above may exhibit neutralizing activity across a broad spectrum of rabies isolates, including terrestrial and bat isolates, such as the bat rabies virus variant "3860 bat."

Antibodies of the invention may, for example, be monoclonal, human, humanized, or chimeric. The antibodies can be full-length antibodies or antibody fragments. The full-length antibodies can be IgG class antibodies, such as full-length IgG1 class antibodies or full-length IgG3 class antibodies. In some instances, the full-length antibody comprises (a) a heavy chain sequence comprising at least 90% sequence identity (e.g., at least 91%, 92%, 93%, 94%, 95%, 96%, 97%, 98%, or 99% sequence identity) to, or the sequence of, the amino acid sequence of SEQ ID NO: 17; (b) a light chain sequence comprising at least 90% sequence identity (e.g., at least 91%, 92%, 93%, 94%, 95%, 96%, 97%, 98%, or 99% sequence identity) to, or the sequence of, the amino acid sequence of SEQ ID NO: 18; or (c) a heavy chain sequence as in (a) and a light chain sequence as in (b). The antibodies can be antibody fragments (e.g., an antibody fragment that binds rabies virus G protein). The antibody fragment may be selected from the group consisting of Fab, Fab'-SH, Fv, scFv, and (Fab')$_2$ fragments. In some instances, the antibody is an IgG antibody (e.g., an IgG1 antibody). An antibody of the invention may have a half-life of ≥3 days (e.g., ≥1 week, e.g., ≥2 weeks, e.g., ≥1 month, e.g., ≥2 months, e.g., ≥3 months, e.g., ≥4 months, e.g., ≥5 months, e.g., ≥6 months).

In a further aspect, an anti-rabies virus antibody according to any of the above embodiments may incorporate any of the features, singly or in combination, as described in Sections 1-5 below.

1. Antibody Affinity

In certain embodiments, an antibody provided herein may have a dissociation constant ($K_D$) of ≤10 µM, ≤1 µM, ≤100 nM, ≤10 nM, ≤1 nM, ≤0.1 nM, or ≤0.01 nM.

In one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, $K_D$ is measured using a BIACORE® surface plasmon resonance assay. For example, an assay using a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one *Langmuir* binding model (BIACORE® Evaluation Software version 3.2) by simultaneously fitting the association and dissociation sensorgrams. The equilibrium dissociation constant ($K_D$) is calculated as the ratio $k_{on}/k_{off}$. See, for example, Chen et al., *J. Mol. Biol.* 293:865-881 (1999). If the on-rate exceeds $10^6 M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, which are known in the art. Also included are diabodies, which have two antigen-binding sites that may be bivalent or bispecific, as is known in the art. Triabodies and tetrabodies are also known. Single-domain antibodies are also antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody (e.g., a human monoclonal antibody (HuMab), e.g., an anti-rabies virus HuMab). Human antibodies can be produced using various techniques known in the art.

In some instances, human antibodies are obtained by cloning the heavy and light chain genes directly from human B cells obtained from a human subject. The B cells are separated from peripheral blood (e.g., by flow cytometry, e.g., FACS), stained for B cell marker(s), and assessed for antigen binding. The RNA encoding the heavy and light chain variable regions (or the entire heavy and light chains) is extracted and reverse transcribed into DNA, from which the antibody genes are amplified (e.g., by PCR) and sequenced. The known antibody sequences can then be used to express recombinant human antibodies against a known target antigen (e.g., rabies virus G protein).

In some instances, human antibodies may be prepared by administering an immunogen (e.g., rabies virus G protein) to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. Human variable regions from intact antibodies generated by such animals may be further modified, for example, by combining with a different human constant region.

In some instances, human antibodies can also be made by hybridoma-based methods, as described in further detail below. Human myeloma and mouse-human heteromyeloma cell lines for the production of human monoclonal antibodies have been described.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Antibody Variants

In certain embodiments, amino acid sequence variants of the anti-rabies virus antibodies of the invention are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

In certain embodiments, antibody variants having one or more amino acid substitutions are provided. Sites of interest for substitutional mutagenesis include the CDRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 1

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g., binding affinity).

Alterations (e.g., substitutions) may be made in CDRs, for example, to improve antibody affinity. Such alterations may be made in CDR "hotspots," i.e., residues encoded by codons that undergo mutation at high frequency during the somatic maturation process, and/or residues that contact antigen, with the resulting variant VH or VL being tested for binding affinity. Affinity maturation by constructing and reselecting from secondary libraries is known in the art. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant VH and VL sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, alternations may be made to the Fc region of an antibody. These alterations can be made alone, or in addition to, alterations to one or more of the antibody variable domains (i.e., VH or VL regions) or regions thereof (e.g., one or more CDRs or FRs). The alterations to the Fc region may result in enhanced antibody effector functions (e.g., complement-dependent cytotoxicity (CDC)), for example, by increasing C1q avidity to opsonized cells. Exemplary mutations that enhance CDC include, for example, Fc mutations E345R, E430G, and S440Y. Accordingly, anti-rabies virus antibodies of the invention may contain one or more CDC-enhancing Fc mutations, which promote IgG hexamer formation and the subsequent recruitment and activation of C1, the first component of complement (see, e.g., Diebolder et al. *Science.* 343: 1260-1263, 2014).

In certain embodiments, alterations of the amino acid sequences of the Fc region of the antibody may alter the half-life of the antibody in the host. Certain mutations that alter binding to the neonatal Fc receptor (FcRn) may extend half-life of antibodies in serum. For example, antibodies that have tyrosine in heavy chain position 252, threonine in position 254, and glutamic acid in position 256 of the heavy chain can have dramatically extended half-life in serum (see, e.g., U.S. Pat. No. 7,083,784).

B. Production of Human Antibodies to Rabies Virus G Protein

1. Immunogens

In general, animals are immunized with virus and/or antigens expressed by rabies virus to produce antibodies. For producing anti-rabies virus antibodies, animals are typically immunized with inactivated rabies virus. Rabies virus can be inactivated, e.g., by chemical treatment and/or lyophilization and several rabies virus vaccines are available commercially.

Anti-rabies virus antibodies that bind and neutralize rabies virus can interact with specific epitopes of rabies virus, for example, rabies virus G glycoprotein. For example, an anti-rabies virus G glycoprotein can bind an epitope within the antigenic site II of rabies virus G protein. In one example, an antibody that binds and neutralizes rabies virus binds to an epitope including amino acid residue(s) Glu33 and/or Cys35 of the rabies virus G glycoprotein. As discussed herein, such an epitope can also be used to identify other antibodies that bind rabies virus with similar, desired properties to that of the antibodies of the invention (e.g., 2B10).

2. Generation of Human Monoclonal Antibodies in HuMAb Mice

Monoclonal antibodies can be produced in a manner not possible with polyclonal antibodies. Polyclonal antisera vary from animal to animal, whereas monoclonal preparations exhibit a uniform antigenic specificity. Murine animal systems are useful to generate monoclonal antibodies, and immunization protocols, techniques for isolating and fusing splenocytes, and methods and reagents for producing hybridomas are well known. Monoclonal antibodies can be produced by a variety of techniques, including conventional monoclonal antibody methodology, e.g., standard somatic cell hybridization techniques.

Although these standard techniques are known, it is desirable to use humanized or human antibodies rather than murine antibodies to treat human subjects, because humans mount an immune response to antibodies from mice and other species. The immune response to murine antibodies is called a human anti-mouse antibody or HAMA response (Schroff, R. et al., *Cancer Res.* 45: 879-885, 1985) and is a condition that causes serum sickness in humans and results in rapid clearance of the murine antibodies from an individual's circulation. The immune response in humans has been shown to be against both the variable and the constant regions of murine immunoglobulins. Human monoclonal antibodies are safer for administration to humans than antibodies derived from other animals and human polyclonal antibodies.

One useful type of animal in which to generate human monoclonal antibodies is a transgenic mouse that expresses human immunoglobulin genes rather than its own mouse immunoglobulin genes. Such transgenic mice, e.g., "HuMAb™" mice, contain human immunoglobulin mini-loci that encode unrearranged human heavy (p and y) and K light chain immunoglobulin sequences, together with targeted mutations that inactivate the endogenous p and K chain loci (see, e.g., Lonberg, N. et al. *Nature* 368(6474): 856-859, 1994, and U.S. Pat. No. 5,770,429, which are incorporated herein by reference in their entirety). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (see, e.g., Lonberg, N. et al., supra; reviewed in Lonberg, N. *Handbook of Experimental Pharmacology* 113:49-101, 1994; Lonberg, N. and Huszar, D., *Intern. Rev. Immunol.*, 13: 65-93, 1995, and Harding, F. and Lonberg, N., *Ann. N.Y. Acad. Sci.*, 764:536-546, 1995, which are incorporated herein by reference in their entirety).

The preparation of such transgenic mice is described in further detail in, for example, Taylor, L. et al., *Nucleic Acids Research*, 20:6287-6295, 1992; Chen, J. et al., *International Immunology* 5: 647-656, 1993; Tuaillon et al., *Proc. Natl. Acad. Sci., USA* 90:3720-3724, 1993; Choi et al., *Nature Genetics*, 4:117-123, 1993; Chen, J. et al., *EMBO J.*, 12: 821-830, 1993; Tuaillon et al., *J. Immunol.*, 152:2912-2920, 1994; Taylor, L. et al., *International Immunology*, 6: 579-591, 1994; and Fishwild, D. et al., *Nature Biotechnology*, 14: 845-851, 1996. See further, U.S. Pat. Nos. 5,545,806; 5,569, 825, 5,625,126, 5,633,425, 5,661,016, 5,770,429, 5,789,650, 5,814,318, 5,874,299 and 5,877,397, all by Lonberg and Kay, and PCT Publication Nos. WO 01/14424, WO 98/24884, WO 94/25585, WO 93/1227, and WO 92/03918, which are incorporated herein by reference in their entirety.

To generate fully human monoclonal antibodies to an antigen, HuMAb mice can be immunized with an immunogen, as described by Lonberg, N. et al., *Nature*, 368(6474): 856-859, 1994; Fishwild, D. et al., *Nature Biotechnology*, 14: 845-851, 1996 and WO 98/24884. Preferably, the mice are 6-16 weeks of age upon the first immunization. For example, a purified preparation of inactivated rabies virus can be used to immunize the HuMAb mice intraperitoneally (IP). To generate antibodies against rabies virus proteins, lipids, and/or carbohydrate molecules, mice can be immunized with live, killed or nonviable inactivated, and/or lyophilized rabies virus. In another embodiment, a rabies virus G glycoprotein, or one or more fragments thereof, can be used as an immunogen.

HuMAb transgenic mice respond best when initially immunized IP with antigen in complete Freund's adjuvant, followed by IP immunizations every other week (up to a total of 6) with antigen in incomplete Freund's adjuvant. The immune response can be monitored over the course of the immunization protocol with plasma samples being obtained by retroorbital bleeds. The plasma can be screened, for example by ELISA or flow cytometry, and mice with sufficient titers of anti-rabies virus human immunoglobulin can be used for fusions. Mice can be boosted intravenously with antigen 3 days before sacrifice and removal of the spleen. It is expected that multiple fusions for each antigen may need to be performed. Several mice are typically immunized for each antigen.

The mouse splenocytes can be isolated and fused with PEG to a mouse myeloma cell line based upon standard protocols. The resulting hybridomas are then screened for the production of antigen-specific antibodies. For example, single cell suspensions of splenic lymphocytes from immunized mice are fused to one-sixth the number of P3X63-Ag8.653 nonsecreting mouse myeloma cells (ATCC, CRL 1580) with 50% PEG. Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1× HAT (Sigma; the HAT is added 24 hours after the fusion). After two weeks, cells are cultured in medium in which the HAT is replaced with HT. Supernatants from individual wells are then screened by ELISA for human anti-rabies virus monoclonal IgM and IgG antibodies. The antibody secreting hybridomas are re-plated, screened again, and if still positive for human IgG, anti-rabies virus monoclonal antibodies, can be subcloned at least twice by limiting dilution. The stable subclones are then cultured in vitro to generate small amounts of antibody in tissue culture medium for characterization.

In one embodiment, the transgenic animal used to generate human antibodies to the rabies virus contains at least one, typically 2-10, and sometimes 25-50 or more copies of the transgene described in Example 12 of WO 98/24884 (e.g., pHC1 or pHC2) bred with an animal containing a single copy of a light chain transgene described in Examples 5, 6, 8, or 14 of WO 98/24884, and the offspring bred with the JH deleted animal described in Example 10 of WO 98/24884, the contents of which are hereby expressly incorporated by reference. Animals are bred to homozygosity for each of these three traits. Such animals have the following genotype: a single copy (per haploid set of chromosomes) of a human heavy chain unrearranged mini-locus (described in Example 12 of WO 98/24884), a single copy (per haploid set of chromosomes) of a rearranged human K light chain construct (described in Example 14 of WO 98/24884), and a deletion at each endogenous mouse heavy chain locus that removes all of the functional $J_H$ segments (described in Example 10 of WO 98/24884). Such animals are bred with mice that are homozygous for the deletion of the $J_H$ segments (Examples 10 of WO 98/24884) to produce offspring that are homozygous for the $J_H$ deletion and hemizygous for the human heavy and light chain constructs. The resultant animals are injected with antigens and used for production of human monoclonal antibodies against these antigens.

The B cells isolated from such an animal are monospecific with regard to the human heavy and light chains because they contain only a single copy of each gene. Furthermore, they will be monospecific with regard to human or mouse heavy chains because both endogenous mouse heavy chain gene copies are nonfunctional by virtue of the deletion spanning the $J_H$ region introduced as described in Examples 9 and 12 of WO 98/24884. Furthermore, a substantial fraction of the B cells will be mono specific with regards to the human or mouse light chains, because expression of the single copy of the rearranged human kappa light chain gene will allelic ally and isotypically exclude the rearrangement of the endogenous mouse kappa and lambda chain genes in a significant fraction of B-cells.

In one embodiment, the transgenic mouse will exhibit immunoglobulin production with a significant repertoire, ideally substantially similar to that of a native mouse. Thus, for example, in embodiments where the endogenous Ig genes have been inactivated, the total immunoglobulin levels will range from about 0.1 to 10 mg/ml of serum, e.g., 0.5 to 5 mg/ml, or at least about 1.0 mg/ml. When a transgene capable of effecting a switch to IgG from IgM has been introduced into the transgenic mouse, the adult mouse ratio of serum IgG to IgM is preferably about 10:1. The IgG to IgM ratio will be much lower in the immature mouse. In general, greater than about 10%, e.g., about 40% to 80% of the spleen and lymph node B cells will express exclusively human IgG protein.

The repertoire in the transgenic mouse will ideally approximate that shown in a non-transgenic mouse, usually at least about 10% as high, preferably 25% to 50% or more as high. Generally, at least about a thousand different immunoglobulins (ideally IgG), preferably $10^4$ to $10^6$ or more, will be produced, depending primarily on the number of different V, J, and D regions introduced into the mouse genome. Typically, the immunoglobulins will exhibit an affinity for pre-selected antigens of at least about $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M, or greater, e.g., up to $10^{-15}$ M or more.

HuMAb mice can produce B cells that undergo class-switching via intra-transgene switch recombination (cis-switching) and express immunoglobulins reactive with the rabies virus. The immunoglobulins can be human sequence antibodies, wherein the heavy and light chain polypeptides are encoded by human transgene sequences, which may include sequences derived by somatic mutation and V region recombinatorial joints, as well as germline-encoded sequences. These human sequence immunoglobulins can be referred to as being substantially identical to a polypeptide sequence encoded by a human VL or VH gene segment and a human JL or JL segment, even though other non-germline sequences may be present as a result of somatic mutation and differential V-J and V-D-J recombination joints. With respect to such human sequence antibodies, the variable regions of each chain are typically at least 80 percent encoded by human germline V, J, and, in the case of heavy chains, D, gene segments. Frequently at least 85 percent of the variable regions are encoded by human germline sequences present on the transgene. Often 90 or 95 percent or more of the variable region sequences are encoded by human germline sequences present on the transgene. However, since non-germline sequences are introduced by somatic mutation and VJ and VDJ joining, the human sequence antibodies will frequently have some variable region sequences (and less frequently constant region sequences) that are not encoded by human V, D, or J gene segments as found in the human transgene(s) in the germline of the mice. Typically, such non-germline sequences (or individual nucleotide positions) will cluster in or near CDRs, or in regions where somatic mutations are known to cluster.

The human sequence antibodies that bind to the rabies virus can result from isotype switching, such that human antibodies comprising a human sequence gamma chain (such as gamma 1, gamma 2, or gamma 3) and a human sequence light chain (such as K) are produced. Such isotype-switched human sequence antibodies often contain one or more somatic mutation(s), typically in the variable region and often in or within about 10 residues of a CDR as a result of affinity maturation and selection of B cells by antigen, particularly subsequent to secondary (or subsequent) antigen challenge.

Anti-rabies virus antibodies can also be raised in other mammals, including non-transgenic mice, humans, rabbits, and goats. Indeed, it is specifically contemplated that antibodies can also be derived from B cells of immunized or infected subjects as an alternative to using HuMAb mice.

3. Production and Modification of Antibodies

Anti-rabies virus antibodies or portions thereof useful in the present invention can also be recombinant antibodies produced by host cells transformed with DNA encoding immunoglobulin light and heavy chains of a desired antibody. Recombinant antibodies may be produced by known genetic engineering techniques, as described, for example, in U.S. Pat. No. 4,816,567, which is herein incorporated by reference in its entirety. For example, recombinant antibodies can be produced by cloning a nucleotide sequence, e.g., a cDNA or genomic DNA, encoding the immunoglobulin light and heavy chains of the desired antibody. The nucleotide sequence encoding those polypeptides may be manipulated if desired (e.g., cloned to switch from one isotype to another, e.g., cloned to switch from an IgG3 class isotype to an IgG1 class isotype), and is then inserted into an expression vector so that both genes are operatively linked to their own transcriptional and translational expression control sequences. The expression vector and expression control sequences are chosen to be compatible with the expression host cell used. Typically, both genes are inserted into the same expression vector. Prokaryotic or eukaryotic host cells may be used.

Expression in eukaryotic host cells is preferred because such cells are more likely than prokaryotic cells to assemble and secrete a properly folded and immunologically active antibody. However, any antibody produced that is inactive due to improper folding can be renatured according to well known methods (Kim and Baldwin, *Ann. Rev. Biochem.* 51: 459-89, 1982, which is herein incorporated by reference in its entirety). It is possible that the host cells will produce portions of intact antibodies, such as light chain dimers or heavy chain dimers, which also are antibody homologs according to the present invention.

The antibodies described herein also can be produced in a host cell transfectoma using, for example, a combination of recombinant DNA techniques and gene transfection methods as is well known in the art (Morrison, S., *Science,* 229: 1202, 1985, which is herein incorporated by reference in its entirety). For example, in one embodiment, the gene(s) of interest, e.g., human antibody genes, can be ligated into an expression vector such as a eukaryotic expression plasmid such as used in a GS gene expression system disclosed in WO 87/04462, WO 89/01036, and EP 338 841, which are herein incorporated by reference in their entirety, or in other expression systems well known in the art. In another example, the antibody genes of interest can be selected (e.g., by methotrexate selection) in eukaryotic host cells, such as CHO cells. The purified plasmid with the cloned antibody genes can be introduced in eukaryotic host cells such as CRO-cells or NSO-cells or alternatively other eukaryotic cells like a plant derived cells, fungi, or yeast cells. The method used to introduce these genes can be any method described in the art, such as electroporation, lipofectine, lipofectamine, transfection (e.g., calcium chloride-mediated), or ballistic transfection, in which cells are bombarded with microparticles carrying the DNA of interest (Rodin, et al. *Immunol. Lett.* 74(3): 197-200, 2000, which is herein incorporated by reference in its entirety). After introducing these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells using standard techniques.

It will be understood that variations on the above procedures are useful in the present invention. For example, it may be desired to transform a host cell with DNA encoding either the light chain or the heavy chain (but not both) of an antibody. Recombinant DNA technology may also be used to remove some or all of the DNA encoding either or both of the light and heavy chains that is not necessary for binding, e.g., the constant region may be modified by, for example, deleting specific amino acids. The molecules expressed from such truncated DNA molecules are useful in the methods described herein. In addition, bifunctional antibodies can be produced in which one heavy and one light chain bind to a rabies virus, and the other heavy and light chain are specific for an antigen other than the rabies virus, or another epitope of the rabies virus.

As described above, also within the scope of the invention are antibodies in which specific amino acids have been substituted, deleted, or added. In particular, preferred antibodies have amino acid substitutions in the framework region, such as to improve binding to the antigen. For example, a selected, small number of acceptor framework residues of the immunoglobulin chain can be replaced by the corresponding donor amino acids. Preferred locations of the substitutions include amino acid residues adjacent to the CDR, or which are capable of interacting with a CDR (see, e.g., U.S. Pat. No. 5,585,089, which is herein incorporated by reference in its entirety). Criteria for selecting amino acids from the donor are described in U.S. Pat. No. 5,585,089 (e.g., col. 12-16). The acceptor framework can be a mature human antibody framework sequence or a consensus sequence. As desired, the Fc region of antibodies of the invention can be altered to modulate effector function(s) such as, for example, complement binding and/or Fc receptor binding. Criteria and subsets of framework alterations and/or constant regions suitable for alteration (by, e.g., substitution, deletion, or insertion) are described in U.S. Pat. Nos. 6,548,640; 5,859,205; 6,632,927; 6,407,213; 6,054,297; 6,639,055; 6,737,056; and 6,673,580, which are herein incorporated by reference in their entirety.

An anti-rabies virus antibody, or an antigen-binding portion thereof, can be derivatized or linked to another functional molecule (e.g., another peptide or protein). For example, an antibody can be functionally linked (by chemical coupling, genetic fusion, non-covalent association or otherwise) to one or more other molecular entities, such as another antibody, a detectable agent, a cytotoxic agent, a pharmaceutical agent, and/or a protein or peptide that can mediate association with another molecule (such as a streptavidin core region or a polyhistidine tag). One type of derivatized antibody (or fragment thereof) is produced by crosslinking two or more of such proteins (of the same type or of different types). Suitable crosslinkers include those that are heterobifunctional, having two distinct reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or fragment thereof can be derivatized (or labeled) include fluorescent compounds, various enzymes, prosthetic groups, luminescent materials, bioluminescent materials, and radioactive materials. Exemplary fluorescent detectable agents include fluorescein, fluorescein isothiocyanate, rhodamine, and, phycoerythrin. A protein or antibody can also be derivatized with detectable enzymes, such as alkaline phosphatase, horseradish peroxidase, 13-galactosidase, acetylcholinesterase, glucose oxidase and the like. When a protein is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A protein can also be derivatized with a prosthetic group (e.g., streptavidin/biotin and avidin/biotin). For example, an antibody can be derivatized with biotin, and detected through indirect measurement of avidin or streptavidin binding.

Labeled proteins and antibodies can be used, for example, diagnostically and/or experimentally in a number of contexts, including (i) to isolate a predetermined antigen by standard techniques, such as affinity chromatography or immunoprecipitation; and (ii) to detect a predetermined antigen (e.g., a rabies virus, or rabies virus protein (e.g., a rabies virus G protein), carbohydrate, or lipid, or combination thereof, e.g., in a cellular lysate or a patient sample) in order to monitor virus and/or protein levels in tissue as part of a clinical testing procedure, e.g., to determine the efficacy of a given treatment regimen.

Any of the above protein derivatizing/labeling techniques can also be employed on a viral target, for example, a rabies protein, such as a G glycoprotein or fragment(s) thereof.

C. Screening Methods

Anti-rabies virus antibodies can be characterized for binding to the rabies virus by a variety of known techniques. Antibodies are typically characterized by ELISA first. Briefly, micro titer plates can be coated with the target antigen in PBS, for example, the rabies virus or G glycoprotein or portion thereof, and then blocked with irrelevant proteins such as bovine serum albumin (BSA) diluted in PBS. Dilutions of plasma from mice immunized with the target antigen, for example, a rabies vaccine, are added to each well and incubated for 1-2 hours at 37° C. The plates are washed with PBS/Tween 20 and then incubated with a goat-anti-human IgG Fc-specific polyclonal reagent conjugated to alkaline phosphatase for I hour at 37° C. After washing, the plates are developed with ABTS substrate, and analyzed at Of) of 405. Preferably, mice which develop the highest titers will be used for fusions.

An ELISA assay as described above can be used to screen for antibodies and, thus, hybridomas that produce antibodies that show positive reactivity with rabies virus. Hybridomas that produce antibodies that bind, preferably with high affinity, to rabies virus can than be sub cloned and further characterized. One clone from each hybridoma, which retains the reactivity of the parent cells (by ELISA), can then be chosen for making a cell bank, and for antibody purification.

To purify the anti-rabies virus antibodies, selected hybridomas can be grown in roller bottles, two-liter spinner-flasks or other culture systems. Supernatants can be filtered and concentrated before affinity chromatography with protein A-Sepharose (Pharmacia, Piscataway, N.J.) to purify the protein. After buffer exchange to PBS, the concentration can be determined by spectrophotometric methods.

To determine if the selected monoclonal antibodies bind to unique epitopes, each antibody can be biotinylated using commercially available reagents (Pierce, Rockford, Ill.). Biotinylated MAb binding can be detected with a streptavidin labeled probe. Anti-rabies virus antibodies can be further tested for reactivity with the rabies virus or rabies virus protein by immunoprecipitation or immunoblot.

Particular antibodies of the invention are characterized as binding to one or more epitope of a rabies G glycoprotein, such as antigenic site II of the rabies G glycoprotein, which includes other antigenic sites such as antigenic site I, antigenic site III, and antigenic site minor A.

Other assays to measure activity of the anti-rabies virus antibodies include neutralization assays. In vitro neutralization assays can measure the ability of an antibody to inhibit a cytopathic effect, infectivity, or presence of a virus on or in cells in culture. Such in vitro neutralization assays include the Rapid Fluorescent Foci Inhibition Test (RFFIT) assay, described below and exemplified the Examples described herein. In vivo neutralization or survival assays can be used to measure rabies virus neutralization as a function of reduced morbidity and/or mortality in an appropriate animal model.

D. Methods of Treatment and Pharmaceutical Compositions

Antibodies and antibody fragments of the present invention have in vitro and in vivo therapeutic, prophylactic, and diagnostic utilities. For example, these antibodies can be administered to cells in culture, e.g., in vitro or ex vivo, or in vivo, to an subject, preferably a human subject, to treat, inhibit, prevent relapse, and/or diagnose rabies virus and disease associated with rabies.

In one aspect, the invention features a method of treating a subject having a rabies virus infection or exposed to an environment in which the subject would be at substantial risk of acquiring a rabies virus infection, wherein the method comprises administering a therapeutically effective amount of a monoclonal antibody (e.g., a human monoclonal antibody) that specifically binds to rabies virus (e.g., the G glycoprotein of rabies virus), such as antibody 2B10 or an antibody sharing the same or substantially the same CDRs or VH/VL domain as the 2B10 antibody, or a pharmaceutical composition thereof, thereby treating the subject. Therefore, in some instances, the antibodies provided herein are useful for post-exposure treatment of a subject. And in other instances, the antibodies provided herein are useful for prophylactic treatment of a subject. In some instances, a subject can be considered at risk of a rabies virus infection if the subject is in a geographic region in which rabies fatalities or rabies virus exposures are significant. In other instances, subject can be considered at risk of a rabies virus infection if the subject had travelled, or will travel, to a geographic region in which rabies fatalities or rabies virus exposures are significant.

Antibodies of the invention can be used either alone or in combination with other agents in a therapy. For instance, an antibody of the invention may be co-administered with at least one additional therapeutic agent (e.g., another anti-rabies virus antibody, such as 17C7, a rabies vaccine, and/or HRIG). Such combination therapies encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the first anti-rabies virus antibody and administration of an additional therapeutic agent (e.g., a rabies vaccine and/or second anti-rabies virus antibody) occur within about one month, or within about one, two or three weeks, or within about one, two, three, four, five, or six days, of each other. The administered anti-rabies virus antibody and/or additional therapeutic agent(s) can be dosed on multiple days in a particular regimen depending on the circumstances (e.g., a post-exposure subject maybe dosed at days 0, 3, 7, 14, and 28, in one example of post-exposure prophylactic treatment).

An anti-rabies virus antibody provided herein can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. In certain instances, antibody genes (e.g., genes encoding any one or more of the anti-rabies virus antibodies of the invention could be administered as a gene therapy to produce the one or more anti-rabies virus antibodies in the subject using either DNA vectors or viral vectors (e.g., rAAV vectors, lentiviral vectors, etc.). Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, such as a rabies virus infection, the appropriate dosage of an antibody of the invention (when used alone or in combination with one or more other additional therapeutic agents) will depend on the type of disease to be prevented/treated, the duration of effective antibody concentration required, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

As a general proposition, the therapeutically effective amount of the anti-rabies virus antibody administered to human will be in the range of about 0.001 to about 100 mg/kg of patient body weight whether by one or more administrations. In some embodiments, the antibody used is about 0.001 to about 45 mg/kg, about 0.001 to about 40 mg/kg, about 0.01 to about 35 mg/kg, about 0.001 to about 30 mg/kg, about 0.001 to about 25 mg/kg, about 0.001 to about 20 mg/kg, about 0.001 to about 15 mg/kg, about 0.001 to about 10 mg/kg, about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.1 to about 10 mg/kg, or about 1 to about 10 mg/kg administered one (single administration) or more times (multiple administrations, e.g., daily administrations). In some embodiments, the antibody used is about 0.001 to about 45 IU/kg, about 0.001 to about 40 IU/kg, about 0.01 to about 35 IU/kg, about 0.001 to about 30 IU/kg, about 0.001 to about 25 IU/kg, about 0.001 to about 20 IU/kg, about 0.001 to about 15 IU/kg, about 0.001 to about 10 IU/kg, about 0.01 to about 45 IU/kg, about 0.01 to about 40 IU/kg, about 0.01 to about 35 IU/kg, about 0.01 to about 30 IU/kg, about 0.01 to about 25 IU/kg, about 0.01 to about 20 IU/kg, about 0.01 to about 15 IU/kg, about 0.01 to about 10 IU/kg, about 0.1 to about 10 IU/kg, or about 1 to about 10 IU/kg administered one (single administration) or more times (multiple administrations, e.g., daily administrations). In one embodiment, an anti-rabies virus antibody described herein is administered to a human at a dose of about 1 mg, about 10 mg, about 20 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg. In one embodiment, an anti-rabies virus antibody described herein is administered to a human at a dose of about 1 IU, about 10 IU, about 20 IU, about 50 IU, about 100 IU, about 200 IU, about 300 IU, about 400 IU, about 500 IU, about 600 IU, about 700 IU, about 800 IU, about 900 IU, about 1000 IU, about 1100 IU, about 1200 IU, about 1300 IU or about 1400 IU. The dose may be administered as a single dose or as multiple doses (e.g., 2 or 3 doses), such as infusions. For repeated administrations over several days or longer, depending on the condition, the treatment would generally be sustained until a desired suppression of disease symptoms occurs. One exemplary dosage of the antibody would be in the range from about 0.01 mg/kg to about 10 mg/kg. Such doses may be administered intermittently, for example, every week or every three weeks (e.g., such that the patient receives from about two to about twenty, or, for example, about six doses of the anti-rabies virus antibody). An initial higher loading dose, followed by one or more lower doses may be administered. The progress of this therapy is easily monitored by conventional techniques and assays.

Actual dosage levels of the active ingredients in the pharmaceutical compositions of the present invention may be varied so as to obtain an amount of the active ingredient which is effective to achieve the desired therapeutic response and duration for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian can start doses of the compounds of the invention employed in the pharmaceutical composition at levels lower than that required in order to achieve the desired therapeutic effect and gradually increase the dosage until the desired effect is achieved. In general, a suitable daily dose of compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. The liposomes may comprise one or more moieties which are selectively transported into specific cells or organs, thus enhance targeted drug delivery. Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134), different species of which may comprise the formulations of the inventions, as well as components of the invented molecules; p 120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273. In one embodiment of the invention, the therapeutic compounds of the invention are formulated in liposomes; in a more preferred embodiment, the liposomes include a targeting moiety. The composition must be fluid to the extent that easy syringability exists. It must be stable under the conditions of manufacture and storage and must be preserved against the contaminating action of microorganisms such as bacteria and fungi.

In some instances, the antibody-based therapy may be combined with an additional therapy for more efficacious treatment (e.g., additive or synergistic treatment) of the subject. Accordingly, subjects treated with antibodies of the invention can be additionally administered (prior to, simultaneously with, or following administration of a HuMab anti-rabies virus antibody of the invention) with another therapeutic agent which enhances or augments the therapeutic effect of the human antibodies.

Additionally, the antibodies provided herein can be used on cells in culture, e.g., in vitro or ex vivo. For example, cells can be cultured in vitro in culture medium and the contacting step can be effected by adding the anti-rabies virus antibody or fragment thereof, to the culture medium. The methods can be performed on virions or cells present in a subject, as part of an in vivo (e.g., therapeutic or prophylactic) protocol. For in vivo embodiments, the contacting step is effected in a subject and includes administering an anti-rabies virus antibody or fragment thereof to the subject under conditions effective to permit binding of the antibody, or fragment, to a rabies virus or any portion thereof present in the subject, e.g., in or around a wound or on or near the infection site. Suitable dosages of the molecules used will depend on the age and weight of the subject and the particular drug used. The antibody molecules can be used as competitive agents for ligand binding to inhibit or reduce an undesirable interaction, e.g., to inhibit binding and/or infection of rabies virus of cells.

An anti-rabies virus antibody, or antigen-binding fragment thereof, such as the HuMab 2B10, can be administered in combination with other anti-rabies virus antibodies (e.g., other monoclonal antibodies, such as the HuMab 17C7 (see U.S. Pat. Nos. 7,727,532 and 8,226,952) or human rabies immunoglobulin (HRIG). Therefore, in some embodiments, the subject is administered at least one dose of the antibody or the pharmaceutical composition and subsequently administered at least one (e.g., at least one, two three, four, or five doses of HRIG or a pharmaceutical composition thereof, such as HRIG at a dosage of about 20 IU/kg. As described in the Examples below, combinations of anti-rabies virus antibodies that include the 2B10 antibody (e.g., a combination of 2B10 and 17C7) can provide potent inhibition of the rabies virus, especially, for example, particular rabies street isolates that are not capable of being neutralized efficiently by treatment with a single anti-rabies virus antibody, such as monotherapy with 17C7 or HRIG. Characteristic rabies virus isolates for which the antibodies of the invention are suitable for treating, detecting, diagnosing and the like include, for example, CVS-11 isolate, ERA isolate, Pasteur virus isolate, gray fox (Texas) isolate, gray fox (Arizona) isolate, artic fox (Arkansas) isolate, skunk (North Central) isolate, skunk (South Central) isolate, raccoon isolate, coyote (Texas) isolate, dog (Texas) isolate, bat (*Lasiurus borealis*; Tennessee) isolate, bat (*Eptesicus fuscus*-*Myotis* spp.; Colorado) isolate, bat (*Myotis* spp.; Washington) isolate, bat (*Lasiurus cinereus*; Arizona) isolate, bat (*Pipistrellus subflavus*; Alabama) isolate, bat (*Tadarida brasiliensis*; Alabama) isolate, bat (*Lasionycetris noctivagans*; Washington) isolate, bat (*Eptesicus fuscus*; Pennsylvania) isolate, mongoose (New York/Puerto Rico) isolate, dog (Argentina) isolate, dog (Sonora) isolate, dog (Gabon) isolate, dog (Thai) isolate, Peruvian bat isolate, and combinations thereof.

It is understood that any of the agents of the invention, for example, anti-rabies virus antibodies, or fragments thereof, can be combined, for example in different ratios or amounts, for improved therapeutic effect. Indeed, the agents of the invention can be formulated as a mixture, or chemically or genetically linked using art recognized techniques thereby resulting in covalently linked antibodies (or covalently linked antibody fragments), having anti-rabies binding properties, for example, multi-epitope binding properties to, for example, rabies virus G glycoprotein. The combined formulation may be guided by a determination of one or more parameters such as the affinity, avidity, or biological efficacy of the agent alone or in combination with another agent. The agents of the invention can also be administered in combination with other agents that enhance access, half-life, or stability of the therapeutic agent in targeting, clearing, and/or sequestering rabies virus or an antigen thereof.

Such combination therapies are preferably additive and even synergistic in their therapeutic activity, e.g., in the inhibition, prevention, infection, and/or treatment of rabies virus-related disease or disorders. Administering such combination therapies can decrease the dosage of the therapeutic agent (e.g., antibody or antibody fragment mixture, or cross-linked or genetically fused bispecific antibody or antibody fragment) needed to achieve the desired effect.

Immunogenic compositions that contain an immunogenically effective amount of a rabies virus component, for example, rabies virus G glycoprotein or fragments thereof, are also provided by the present invention, and can be used in generating anti-rabies virus antibodies. Immunogenic epitopes in a rabies virus protein sequence can be identified as described herein or according to methods known in the art, and proteins or fragments containing those epitopes can be delivered by various means, in a vaccine composition. Suitable compositions can include, for example, lipopeptides (e.g., Vitiello et al., *J. Clin. Invest.* 95:341 (1995)), peptide compositions encapsulated in poly (DL-lactide-coglycolide) ("PLG") micro spheres (see, e.g., Eldridge et al., *Molec. Immunol.* 28:287-94 (1991); Alonso et al., *Vaccine* 12:299-306 (1994); Jones et al., *Vaccine* 13:675-81 (1995)), peptide compositions contained in immune stimulating complexes (ISCOMS) (see, e.g., Takahashi et al., *Nature* 344: 873-75 (1990); Hu et al., *Clin. Exp. Immunol.* 113:235-43 (1998)), and multiple antigen peptide systems (MAPs) (see, e.g., Tam, *Proc. Natl. Acad. Sci. U.S.A.* 85:5409-13 (1988); Tam, *J. Immunol. Methods* 196:17-32 (1996)).

The anti-rabies antibody (e.g., 2B10) or antibodies (e.g., 2B10 and 17C7) can be administered in combination with other agents, such as compositions to treat rabies virus-mediated disease. For example, therapeutics that can be administered in combination with anti-rabies antibodies include antiviral agents, serum immunoglobulin, and/or vaccines for treating, preventing, or inhibiting rabies (for example, vaccines such as RABIVAX (Serum Institute of India), RABAVERT™ (Chiron), Rabies vaccine adsorbed (Bioport), and IMOVAX® Rabies (Aventis) and/or immunoglobulins, such as BAYRAB™ (Bayer) and IMOGAM™ Rabies-HT (Aventis). The antibody can be administered before, after, or contemporaneously with a rabies virus vaccine.

A pharmaceutical composition including one or more anti-rabies antibodies of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Useful carriers that can be used with compositions of the invention are well known, and include, for example, thyroglobulin, albumins such as human serum albumin, tetanus toxoid, polyamino acids such as poly L-lysine, poly L-glutamic acid, influenza, hepatitis B virus core protein, and the like. The compositions can contain a physiologically tolerable (i.e., acceptable) diluent such as water, or saline, typically phosphate buffered saline. The compositions and vaccines also typically include an adjuvant. Adjuvants such as incomplete Freund's adjuvant, aluminum phosphate, aluminum hydroxide, or alum are examples of materials well known in the art. Additionally, CTL responses can be primed by conjugating target antigens, for example a rabies virus protein(s) (or fragments, inactive derivatives or analogs thereof) to lipids, such as palmitoyl-S-glycerylcysteinyl-seryl-serine ($P_3CSS$). Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions of the invention also can be administered in combination therapy, i.e., combined with other agents. For example, the combination therapy can include a composition of the present invention with at least one or more additional therapeutic agents as necessary for the particular indication (e.g., rabies virus infection) being treated.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions.

Sustained-release preparations may be prepared. Suitable examples of sustained-release preparations include semipermeable matrices of solid hydrophobic polymers containing the antibody, which matrices are in the form of shaped articles, for example, films, or microcapsules.

The formulations to be used for in vivo administration are generally sterile. Sterility may be readily accomplished, e.g., by filtration through sterile filtration membranes. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof. Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, such as TWEEN® 80. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Alternatively, genes encoding the anti-rabies virus antibodies of the invention may be delivered directly into the subject for expression rather than administering purified antibodies for prevention or therapy. For example, viral vectors, such as recombinant viruses, can be used to deliver the heavy and light chain genes. In one example, rAAV virus particles can be used to deliver anti-HIV monoclonal antibodies (Balazs et al. *Nature.* 481: 81, 2012). Antibody genes could also be effectively delivered by electroporation of muscle cells with plasmid DNA containing heavy and/or light chain genes (e.g., VH and/or VL genes) (Muthumani et al. *Hum Vaccin Immunother.* 10: 2253, 2013). Lentivirus vectors or other nucleic acids (e.g., RNA) capable of delivering transgenes could also be used to delivery antibody genes to establish serum antibody levels capable of prevention.

E. Methods and Compositions for Diagnostics and Detection

In certain embodiments, any of the anti-rabies virus antibodies of the invention are useful for in vitro or in vivo detection of the presence of rabies virus (specifically, the G glycoprotein of rabies virus) in a biological sample. The term "detecting" as used herein encompasses quantitative or qualitative detection. In certain embodiments, a biological sample comprises a cell or tissue.

In one embodiment, an anti-rabies virus antibody for use in a method of diagnosis (e.g., diagnosis of a rabies virus infection) or detection (e.g., detection of a rabies virus infection) is provided. In a further aspect, a method of detecting the presence of rabies virus (specifically, the G glycoprotein of rabies virus) in a biological sample (e.g., a serum sample) is provided. In certain embodiments, the method comprises contacting the biological sample with an anti-rabies virus antibody as described herein (e.g., the 2B10 anti-rabies virus HuMab) under conditions permissive for binding of the anti-rabies virus antibody to rabies virus (specifically, the G glycoprotein of rabies virus), and detecting whether a complex is formed between the anti-rabies virus antibody and rabies virus target. Such method may be an in vitro or in vivo method. The method therefore allows the screening of samples for the presence/exposure of rabies virus. As noted above, the anti-rabies antibodies provided herein can also be used diagnostically to monitor levels of the virus, e.g., in tissue as part of a clinical testing procedure, e.g., to, for example, determine the efficacy of a given treatment regimen. In addition, rabies virus epitopes, for example, G glycoprotein epitopes (linear, conformational, or combinations thereof) can be used as immunogens or as targets to identify neutralizing anti-rabies binding molecules, including, for example, human serum, polyclonal antibodies, monoclonal antibodies, or fragments thereof.

In certain embodiments, labeled anti-rabies virus antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Articles of Manufacture

In another aspect of the invention, an article of manufacture (e.g., a kit) containing materials useful for the treatment, prevention, and/or diagnosis of the rabies virus infection described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody (e.g., 2B10) provided herein. The article of manufacture (e.g., kit) can further contain one or more additional reagents, such as a second, different anti-rabies virus antibody having a complementary activity that binds to an epitope on rabies virus (e.g., an eptiope on the G glycoprotein of rabies virus) that is distinct from the epitope to which the first anti-rabies virus antibody binds (e.g., 17C7). The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition (e.g., rabies). Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Other embodiments of the present invention are described in the following Examples. The present invention is further illustrated by the following examples which should not be construed as further limiting. The contents of Sequence Listing, figures and all references, patents and published patent applications cited throughout this application are expressly incorporated herein by reference.

III. Examples

The following are examples of methods and compositions of the invention. It is understood that various other embodiments may be practiced, given the general description provided above.

Example 1. Materials and Methods

The invention is further described in the following examples, which do not limit the scope of the invention described in the claims.

Mouse Immunization and Isolation of Hybridomas

HuMab mice (Medarex) are transgenic mice containing human immunoglobulin genes and inactivated mouse heavy chain genes and kappa light chain genes. HuMab mice were typically injected with a ~1/10 of a human dose of a commercially available rabies vaccine (IMOVAX®). A rabies envelope glycoprotein ELISA was used to measure serum responses and animals were sacrificed when serum responses were considered maximal. Hybridomas were generated by fusion of splenocytes and partner cells (P3X63Ag8.653 mouse myeloma cells). Hybridomas were initially screened for cells secreting human IgGs using a human IgG capture ELISA. Positive antibodies were purified from hybridoma cultures by protein A Sepharose chromatography (Amersham). The human IgG's were further screened in a rabies G glycoprotein specific ELISA. Antibodies that bound rabies G glycoprotein were further tested in RFFITs against RABV virus stocks.

Rapid Fluorescent Focus Inhibition Test (RFFIT)

The Rapid Fluorescent Focus Inhibition Test (RFFIT) assay was performed as described in the art. The rabies virus strains, street virus isolates, and mouse neuroblastoma cells (MNA) used were all from the Center from Disease Control and Prevention, Atlanta, USA.

Cells and Cell Culture

HEK-293T117 cells, obtained from the ATCC, were grown in Dulbeccos modified Eagle's medium (DMEM) supplemented with 10% fetal bovine serum and 100 IU of penicillin-streptomycin (complete medium) at 37° C. with 5% $CO_2$. Cells were harvested in phosphate buffered saline (PBS) containing 5 mM EDTA.

Cloning of Rabies Glycoproteins

The amino acid sequence of the rabies G protein (ERA strain, Genbank: AF406693) was used to design a codon-optimized version of the rabies glycoprotein gene spanning the full-length glycoprotein from amino acid 1-524. The synthetic gene was cloned into pcDNA3.1Myc/His (Invitrogen) in frame with the c-Myc and 6-histidine (His) tags. These immunotags enabled easy purification and detection. Truncated versions of the tagged glycoprotein-encoding genes were constructed which contained the entire ectodomain (20-439 a.a.). Truncations were made by PCR amplification of the desired fragments from the full length glycoprotein clones followed by restriction digestion and ligation into pcDNA3.1Myc/His (Invitrogen) and verified by DNA sequence analysis.

For the isolation of native genes encoding various strains of rabies G glycoproteins, MNA cells were infected with the desired rabies virus strain(s). RNA was extracted from infected cells or from virions using Trizol reagent. RTPCR was performed in 2 steps. First, cDNA was synthesized using the Ambion Retroscript Kit, and the rabies glycoprotein-encoding genes were then amplified using Turbo Pfu (Stratagene) and rabies virus specific primers. The rabies glycoprotein encoding genes were cloned into the mammalian expression vector pCDNA3.1 Myc/His (Invitrogen) at the HindIII/XbaI sites in frame with the c-Myc and His epitope tags. Recombinant genes encoding rabies glycoprotein mutated at residues classified as antigenic site I, II, III and minor site a were synthesized using site-directed mutagenesis. Overlapping primers containing the desired point mutations were used to amplify full-length mutant glycoprotein genes and the pcDNA3.1Myc/His vector from the previously cloned codon-optimized ERA glycoprotein. The PCR amplified DNA was digested with DpnI to remove the wild type non-amplified starting template, transformed into bacteria, and screened for the intended mutation by sequencing. The full coding sequence of each mutant was confirmed, and the resulting constructs were cloned into pcDNA3.1 Myc/His expression vectors.

Recombinant Glycoprotein Expression

All constructs were transfected into HEK-293T/17 cells using Lipofectamine 2000 (Invitrogen) as described by the manufacturer. Cells were grown to 85% confluence in 150 mm tissue culture dishes in 15 ml of DMEM-10% fetal calf serum (FCS). Amounts of 30 μg of DNA mixed with 75 μl of Lipofectamine were added to the cells, and plates were incubated overnight at 37° C. Media was removed and stored at 24, 48, and 72 hours post-transfection for secreted soluble proteins or discarded for membrane bound proteins.

Cell Surface Staining

Cells transfected with constructs encoding full-length rabies G protein were harvested 48 hours post-transfection and incubated with varying concentration of HuMabs. Binding of the HuMabs was detected by phycoerythrin labeled anti-human IgG (Jackson) and flow cytometry was performed using FACScan with CellQuest software (Becton Dickinson).

Rabies Psuedovirus Analysis

The rabies pseudovirus assay is an in vitro infection/neutralization assay that utilizes rabies pseudotyped viral particles (RABVpp) that are generated with a lentivirus that is devoid of native glycoproteins, and engineered to contain the full length membrane bound rabies G glycoprotein. RABVpp are produced by the co-transfection of the membrane bound rabies G glycoprotein and the lentiviral backbone carrying the luciferase gene. RABVpp specifically infect cell lines such as Baby Hamster Kidney cells (BHK) or 293 cells and can be neutralized by antibodies directed against the rabies envelope glycoproteins (e.g., 17C7/2B10). When the RABVpp infect cells they deliver a luciferase gene whose expression (light) can be measured. The rabies pseudovirus assay is more quantitative with a spectrophotometric output and is safer to perform than a RFFIT test that requires live rabies virus. The assay also has the advantage that the G glycoprotein from any rabies virus of interest can be evaluated, as some natural rabies isolates are difficult to cell culture adapt for the RFFIT assay.

Vaccine Interference Study in Hamsters

Groups of uninfected female Syrian golden hamsters were administered rabies mAbs or HRIG along with rabies vaccine (IMOVAX®, Sanofi Pasteur) according to the WHO Essen schedule for post-exposure prophylaxis. Animals received vaccine and antibody injections in the gastrocnemius muscle of opposite legs. The first day of injections included designated antibody and vaccine followed by additional doses of rabies vaccine on days 3, 7, 14, and 28. Serum samples were obtained from hamsters by the saphenous vein on days 7, 21, 35, and 49. The vaccine dose administered was 5% of the human dose and the dose of HRIG was the human dose of 20 IU/Kg. A monoclonal antibody cocktail (R172), consisting of 17C7 and 2B10, was evaluated at three doses: (1) 1 mg/kg with 17C7: 2B10 at a 1:1 ratio; (2) 0.1 mg/kg with 17C7: 2B10 at a 1:1 ratio; and (3) 1.1 mg/kg with 17C7: 2B10 at a 10:1 ratio. Hamster sera were tested for anti-rabies antibody responses by ELISA and RFFIT. 12-18 animals were included in each test group. Statistical analyses were conducted to compare the difference in antibody concentrations between the test groups.

Post-Exposure Prophylaxis (PEP) in Lethal Challenge Hamster Model

Female Syrian golden hamsters were challenged with rabies virus on day 1 via intramuscular injection in the gastrocnemius or masseter muscle. Twenty-four hours post-challenge (day 0), PEP was initiated with intramuscular injection of designated antibody (R172 or HRIG) at the inoculation site with intramuscular injection of rabies vaccine in the contralateral limb. Additional vaccine doses were administered on days 3, 7, 14, and 28, following the WHO Essen PEP dosing schedule utilized in human exposures. Twelve (12) or 21 animals were included in each treatment group and all animals were observed twice daily for 45 days, including assessment of overall appearance and evaluation for rabies-specific clinical signs, such as seizures, limb paresis, paralysis, or self-mutilation. Animals exhibiting signs of rabies were euthanized. Rabies infection was confirmed in all euthanized animals by direct fluorescent antigen (DFA) staining of the brain stem. A subset of surviving animals (50%) in each test group was also tested by DFA staining to confirm negative staining for rabies virus.

Example 2. Generation of Anti-Rabies Monoclonal Antibody 2B10

Transgenic mice containing human immunoglobulin genes and inactivated mouse heavy and kappa light chain genes (Bristol-Myers Squibb; Medarex HuMab mice) were immunized with 1/10 a human dose of IMOVAX® with the adjuvant RIBI for 10 immunizations. The mouse was fused to P3X mouse cells to create hybridomas. Hybridomas were initially screened for cells secreting human IgGs using a human IgG capture ELISA. 2B10 was identified as a human IgG and then tested in a rabies glycoprotein ELISA to demonstrate binding to rabies virus. Antibodies were prepared from hybridoma 2B10 culture and purified by protein A chromatography. The 2B10 antibodies were then used to neutralize rabies virus in the Rapid Fluorescent Focus Inhibition Test (RFFIT), as described below.

Example 3. Determination of Anti-Rabies Monoclonal Antibody 2B10 Sequence

RT-PCR was performed on the 2B10 hybridoma to determine the sequence of the heavy chain gene of the antibody using a cocktail of primers targeting the variable region of the human heavy chain genes. Forward primers were designed to anneal to all human heavy chain genes expressed in the transgenic mouse, and the reverse primers were specific to human IgG constant genes expressed in the transgenic mice including IgG1 and IgG3. The PCR products were sequenced and the amino acid sequence was deduced. The 2B10 antibody was determined as an IgG3 antibody with VHOrph 44 as the V region, D3-9 as the D region and JH4 as the J region. To efficiently express and purify 2B10 antibody, the variable region of 2B10 antibodies were then cloned into expression vectors with an IgG1 constant region and expressed as an IgG1 antibody.

The 2B10 light chain sequence was determined by mass spectrometry analysis of the light chain protein fragment as a VKIII A27 light chain. Primer sequence specific to the VKIII A27 light chain gene was then used to amplify the light gene of 2B10 to determine the sequence (Table 1).

TABLE 2

Germline information of 2B10

| HuMab | Variable region light chain | | Variable region heavy chain | | |
|---|---|---|---|---|---|
| | VK: | JK: | VH: | D: | JH: |
| 2B10 | A27 | JK2 | VHOrph 44 | D3-9 | JH4 |

Example 4. Identification of 2B10 Binding Site by CVS-11 Escape Mutagenesis

CVS-11 was cultured on MNA cells in the presence of a neutralizing concentration of 2B10 to select for rabies virus that were resistant to neutralization with 2B10. Rapid fluorescence neutralization inhibition test (RFFIT) analysis was done to identify viruses that could grow in the presence of 2B10 (FIG. 1). RNA was isolated from resistant viruses, reverse transcribed, and sequenced to determine the portions of the G glycoprotein that conferred resistance. A single change in position 33 from glutamic acid to lysine (E33K) was identified. Position 33 is part of antigenic site II of the rabies virus G glycoprotein (amino acid residues 33-42 and 198-200 of rabies virus G glycoprotein).

Example 5. Confirmation of E33 by Cell Surface Staining

Escape virus was confirmed by cloning the E33K mutation into the CO-CVS background. Recombinant proteins were expressed in 293T cells. Cells were stained with 2B10 and were tested via FACS. Anti-rabies virus human monoclonal antibody 17C7 (see, e.g., U.S. Pat. Nos. 7,727,532 and 8,226,952, each of which is herein incorporated by reference in its entirety) was used as a positive control. FACS confirmed that 2B10 did not recognize the E33K mutation.

Example 6. Confirmation of Antigenic Site II by Alanine Scanning Mutagenesis

Amino acid residues 33-42 and 198-200 of antigenic site II in surface expressed codon-optimized recombinant G glycoprotein from ERA were changed from their wild-type residues to alanine (alanine scanned) to probe their importance to 2B10 binding. Key changes in position 33 for the laboratory escape mutation (E33K) and *Lasiurus* bat residues (E33D) were also tested. Mutants were transfected to 293T cells and expressed on the cell surface. 2B10 recognition of G glycoproteins was detected by a fluorescent labeled secondary antibody and analyzed by flow cytometry. Individual fluorescence intensity was normalized with anti-rabies virus HuMab 17C7 binding signal as the internal control for G glycoprotein expression. The results are shown below. Residue 33 was confirmed to be critical to 2B10 binding (FIG. 2).

Example 7. 2B10 can Neutralize Rabies Virus Isolates in Very Low Concentrations

The neutralization of laboratory strain CVS-11 was tested by RFFIT analysis. Dilutions of 2B10 were made and added to rabies virus stocks that were used to infect MNA cells. Foci of infection are then identified using fluorescently labeled antibodies to the rabies virus nucleoprotein. Foci are counted and the protein concentration that reduces the number of foci by 50% is recorded ($EC_{50}$). 2B10 neutralized most isolates very strongly with $EC_{50}$ values less than 10 ng. When tested against reference strain CVS-11, 2B10 was more than 200-fold more potent on a weight basis than human rabies immunoglobulin (HRIG) or 17C7 (Table 3).

TABLE 3

$EC_{50}$ Neutralization of CVS-11 by RFFIT

| Virus | Source | HRIG $EC_{50}$ ng/mL | 17C7 $EC_{50}$ ng/mL | 2B10 $EC_{50}$ ng/mL |
|---|---|---|---|---|
| CVS-11 | Lab strain | 1100 | 1000 | 4 |

Example 8. 2B10 can Neutralize a Wide Variety of Rabies Virus Street Isolates

2B10 can neutralize a wide variety of rabies virus street isolates as demonstrated by RFFIT testing. 2B10 clearly requires less protein to effective neutralize rabies virus isolates from a wide variety of terrestrial and bat isolates than HRIG or 17C7 (Table 4).

TABLE 4

$EC_{50}$ Neutralization of street rabies virus by 2B10 by RFFIT

| Virus | Source | HRIG $EC_{50}$ ng/mL | 17C7 $EC_{50}$ ng/mL | 2B10 $EC_{50}$ ng/mL |
|---|---|---|---|---|
| Sonora Dog | Dog, Mexico | 13,800 | 6 | 6 |
| TX SK 4380 | Skunk, Southcentral U.S. (TX) | 12,000 | 6 | 5 |
| PR Mong | Mongoose, Puerto Rico | 10,400 | 7 | 6 |
| AK fox | Fox, Alaska | 6,250 | 5 | 4 |
| RAC | Raccoon, Southeast U.S. | 96,100 | 27 | 30 |
| NC SK | Skunk, North-Central U.S. | 8,930 | 800 | 4 |
| CO Bat EF6938 | *Eptesicus fuscus/Myotis* sp., CO | 19,700 | 182 | 10 |
| C1434 | *Pipistrellus subflavus*, AL | 5,360 | 154 | 8 |
| WA Bat | *Lasionycteris noctivagans*, WA | 28,800 | 870 | 9 |
| Bat EF | *Eptesicus fuscus*, PA | 150,000 | 512 | 15 |
| 3860 Bat | *Pipistrellus hesperus*, CA | 78,100 | >2400000* | 11 |
| Myotis | *Myotis* sp., WA | 28,800 | 4 | 8 |
| DR Brazil | *Desmodus rotundus*, Brazil | 7350 | 222 | 4 |

Example 9. 2B10 in Combination with 17C7 Displays a Broad Breadth of Neutralization When 2B10 is used in combination with the neutralizing rabies HuMab antibody 17C7, the cocktail (R172 of the two antibodies is very effective in neutralizing a broad spectrum of rabies isolates. A mixture of 17C7 and 2B10 in a 1:1 combination (2B10+17C7) was tested against a panel of rabies isolates for neutralization in a RFFIT assay in two separate laboratories with standardized methodology (Tables 5A and 5B). The $EC_{50}$ value reported is the arithmetic mean of multiple assay replicates unless otherwise noted. Strong neutralization was demonstrated against all terrestrial and bat isolates tested. The combination of 2B10 and 17C7 anti-rabies virus antibodies was unexpectedly more effective than HRIG on a weight basis for nearly all viruses tested and was more effective than 17C7 or 2B10 alone in certain cases (e.g., CA Skunk, NC Skunk, Bat 3860, and Bat TN410). The activity of the combination of 2B10 and 17C7 against these viruses shows that the combination is more effective than HRIG on a weight basis and possesses a better breadth of neutralization than either 17C7 or 2B10 alone.

TABLE 5A $EC_{50}$ Neutralization of street rabies virus by 2B10 + 17C7 RFFIT (Test A)

| Virus | Source | HRIG[#] EC50 μg/mL | 17C7 EC50 μg/mL | 2B10 EC50 μg/mL | 2B10 + 17C7 EC50 μg/mL | 17C7 epitope (residue 336 and 346) | 2B10 epitope (residue 33) |
|---|---|---|---|---|---|---|---|
| Sonora Dog | Dog, Mexico | 13.80 | 0.006 | 0.006 | 0.002 | NR | E |
| TX SK 4380 | Skunk, Southcentral U.S. (TX) | 12.00 | 0.006 | 0.005 | 0.004 | NR | E |
| CASK | Skunk, U.S. (CA) | 28.80 | 0.006 | 0.480 | 0.013 | NR | E |
| PR Mong | Mongoose, Puerto Rico | 10.40 | 0.007 | 0.006 | 0.012 | NR | E |
| AK fox | Fox, Alaska | 6.25 | 0.005 | 0.004 | 0.002 | NR | E |
| RAC | Raccoon, Southeast U.S. | 96.10 | 0.027 | 0.030 | 0.009 | SR | E |
| NC SK | Skunk, North-Central U.S. | 8.93 | 0.800 | 0.004 | 0.014 | NK | E |
| CO Bat EF6938 | *Eptesicus fuscus*/ *Myotis* sp., CO | 19.70 | 0.182 | 0.010 | 0.008 | NK | E |
| C1434 | *Pipistrellus subflavus*, AL | 5.36 | 0.154 | 0.008 | 0.009 | NK | E |
| WA Bat | *Lasionycteris noctivagans*, WA | 28.80 | 0.870 | 0.009 | 0.003 | NK | E |
| Bat EF | *Eptesicus fuscus*, PA | 150.00 | 0.512 | 0.015 | 0.008 | DR | E |
| 3860 Bat | *Pipistrellus hesperus*, CA | 78.10 | >2400 | 0.011 | 0.010 | NS | E |
| *Myotis* | *Myotis* sp., WA | 28.80 | 0.004 | 0.008 | 0.005 | NS | E |
| DR Brazil | *Desmodus rotundus*, Brazil | 7.35 | 0.222 | 0.004 | 0.026 | NR | E |
| 1625 Bat | *Lasiurus borealis*, MI | 221.00 | 80.000 | 83.000 | 24.000 | NE | D |
| TN410 | *Lasiurus cinereus*, TN | 53.60 | 8.000 | 222.222 | 12.000 | NE | D |
| TN132 | *Lasiurus borealis*, TN | 150.00 | 414.000 | >2400 | 444.000 | NE | D |
| Texas coyote 323R | Coyote (Texas) | 27.80 | 0.010 | 1.571 | 0.010 | NR | E |
| AZ fox 2400 | Fox (Arizona) | 10.60 | 0.211 | 0.043 | 0.102 | NK | E |
| TX Fox | Fox (Texas) | 35.80 | 0.023 | 0.020 | 0.014 | NK | E |
| CABat | *Myotis thysanodes* (California) | 31.50 | 0.006 | 0.004 | 0.003 | NS | E |
| AZ Bat LC | *Lasiurus cinereus* (Arizona) | 102.40 | 10.000 | 421.800 | 20.000 | NE | D |
| FLBat 769 | *Lasiurus seminolus* (Florida) | 177.30 | 80.240 | >2400 | 354.700 | NE | D |
| TN269 | *Lasiurus borealis* (Tennessee) | 239.60 | 400.0[a] | >2400 | 800.0[a] | NE | D |
| TN33 | *Lasiurus borealis* (Tennessee) | 129.50 | 9.114 | 1622[a] | 4.679 | NE | D |
| VA1340 | *Lasiurus borealis* (Tennessee) | 226.80 | 198.800 | >2400 | 174.200 | NE | D |
| VA399 | *Lasiurus borealis* (Virginia) | 111.90 | 21.950 | 864.0[a] | 44.760 | NE | D |

[a]An isolate for which there were assays with the same starting concentration of antibody showing results above the 50% neutralization threshold in the first well (1:5 dilution) of the RFFIT slide and other assays showing results below the 50% neutralization threshold in the first well of the RFFIT slide. For assays with a result of less than 50% neutralization, the concentration of antibody calculated for the first well (i.e., the starting concentration divided by 5) was used to determine the mean EC50.

[#]HRIG 1 IU/ml = $10^3$ μg/ml

TABLE 5B

EC₅₀ Neutralization of street rabies virus by 2B10 + 17C7 RFFIT (Test B)

| Virus | Source (location) | HRIG $EC_{50}$ μg/mL | 17C7 $EC_{50}$ μg/mL | 2B10 $EC_{50}$ μg/mL | 2B10 + 17C7 $EC_{50}$ μg/mL | 17C7 epitope (residue 336 and 346) | 2B10 epitope (residue 33) |
|---|---|---|---|---|---|---|---|
| Gray fox[b] | Fox (Texas) | 6.00 | 0.0020[c] | <0.0002[c] | 0.0010[c] | NR | E |
| Raccoon | Raccoon (Florida) | 15.00 | 1000.000 | 0.005 | 0.0030[c] | SR | E |
| Skunk (north-central) | Skunk (North-central US) | 26.00 | 7.360 | 0.0050[c] | 0.0150[c] | NK | E |
| Skunk south-central[b] | Skunk (South-central US) | 8.00 | 0.0004[c] | 0.0020[c] | 0.0010[c] | NR | E |
| Eastern pipistrelle | Eastern Pipistrelle (Arkansas) | 58.00 | 143.000 | 0.033 | 0.0320[c] | NK | E |
| Eptesicus fuscus | Eptesicus fuscus (Nebraska) | 9[c] | 0.0020[c] | 0.014 | 0.0003[c] | NK | E |
| Lasiurus cinereus[b] | Lasiurus cinereus (Arkansas) | 46.00 | 10.440 | 116.700 | 5.776 | NE | D |
| SW E fuscus | Eptesicus fuscus (South Dakota) | 24.00 | 675.200 | 0.005 | 0.0070[c] | NK | E |
| Tadarida | Tadarida sp. (Florida) | 15.00 | 1.049 | 0.011 | 0.0030[c] | NK | E |

[b]TCID50 < 30. Acceptable TCID50 range was 30-100 for the challenge virus dose in each assay. If the TCID50 was <30 or >100, results were reported if either of the following criteria were met: (1) If HRIG was tested at 2 different concentrations (e.g., 2 IU/mL and 6 IU/mL) and the measured ratio of the EC50 titers for HRIG at the 2 concentrations was within 50% of the expected ratio, results from all antibody preparations in the assay were accepted as valid; or (2) If HRIG was not tested at 2 different concentrations but an individual antibody was tested at 2 different concentrations and the measured ratio of the EC50 titers for that antibody was within 50% of the expected ratio, results obtained with that antibody in the assay were accepted as valid.
[c]Result from a single RFFIT assay with 50% neutralization titer in the interpretable range of the assay.

Example 10. An In Vitro Rabies Pseudovirus Infection/Neutralization Assay

Since the mechanism of neutralization of 2B10 is to block the interaction of the rabies G-glycoprotein and its receptor, a pseudotyped virus based on the rabies G-glycoprotein can be used to measure potency of the antibodies.

The rabies pseudovirus assay is an in vitro infection/neutralization assay that utilizes rabies pseudotyped viral particles (RABVpp) that are generated from a lentivirus that is devoid of native glycoproteins, and engineered to contain a full-length membrane bound rabies G-glycoprotein and a luciferase gene. RABVpp specifically infect cell lines, such as Baby Hamster Kidney cells (BHK) or 293 cells, and can be neutralized by antibodies directed against the rabies envelope glycoproteins (e.g., 2B10 or 2B10 in combination with 17C7). When the RABVpp infect cells they deliver a luciferase gene whose expression (light) can be measured. The assay also has the advantage that the G glycoprotein from any rabies virus of interest can be evaluated, as some natural rabies isolates are unavailable or difficult to cell culture adapt for the RFFIT assay.

2B10, 17C7, and 2B10 in combination with 17C7 are capable of neutralization of RABVpp with ERA G glycoprotein (FIG. 3). Notably, 2B10, in particular, can neutralize the "Peru Bat" RABVpp, which is resistant to neutralization by 17C7 (FIG. 4). 2B10 can also neutralize the "Florida Raccoon" RABVpp, which is resistant to neutralization to 17C7 (FIG. 5). These studies demonstrate the advantages of 2B10 in neutralizing rabies viruses that are not neutralized by known anti-rabies virus neutralizing antibodies, such as 17C7 and HRIG.

Example 11. Vaccine Interference Studies

Prior studies in humans and animals have shown that immune responses to rabies vaccine, measured by production of anti-rabies antibodies, are reduced when HRIG is given with vaccine compared to vaccine only. Animal experiments were conducted to investigate the effect of 2B10 in combination with 17C7 (R172) on immune responses to rabies vaccine. The experiment was designed according to the WHO Essen recommended post-exposure prophylaxis schedule (FIG. 6A). 12-18 animals were included in each test group, and the average RFFIT titer in each R172 test group was compared to the HRIG plus vaccine control group, as shown in FIG. 6B.

There was a differential effect of R172 antibody cocktail on vaccine responses depending upon the formulation. The R172 (17C7/2B10 1:1 ratio) group at a dose of 1 mg/kg interfered with vaccine responses to a greater extent than HRIG. Comparable responses to HRIG were observed when the dose of the 1:1 cocktail combination was reduced to 0.1 mg/kg or when the 17C7/2B10 10:1 ratio of R172 was given at a total of 1.1 mg/kg ($p<0.05$). Of note, R172 (1:1) at 1 mg/kg and (10:1) at 1.1 mg/kg showed significantly higher neutralizing activity at day 7 compared to HRIG group ($p<0.05$). These experiments identified doses of the 2B10 and 17C7 cocktail (R172) that did not interfere with the rabies vaccine response more than HRIG and were selected to be evaluated in post-exposure prophylaxis experiments.

Example 12. Post-Exposure Prophylaxis (PEP) in Lethal Challenge Hamster Model Hamsters are an established model of rabies pathogenesis and for the evaluation of treatment, including post-exposure prophylaxis (PEP). In this model, hamsters are challenged with rabies virus in the gastrocnemius muscle (or in the masseter muscle) on day 0 and then treated with neutralizing antibodies (2B10+17C7 [R172] or HRIG) at the site of virus challenge and administered 0.05% of a human dose of rabies vaccine in the opposite gastrocnemius muscle on day 1. Additional doses of vaccine are administered on days 3, 7, 14, and 28 to complete the PEP regimen (FIG. 7A). Animals receiving PEP are monitored for 45 days for signs or symptoms of rabies. Animals that die during the study or are euthanized for clinical signs of suspected rabies are tested for rabies virus post-mortem by direct fluorescent antibody staining.

The ability of the R172 mAb cocktail to protect hamsters exposed to a lethal rabies virus challenge was evaluated using the terrestrial rabies variant Texas coyote 323R. The Texas coyote 323R isolate glycoprotein contains an "E33 N336 R346" epitope variant, which is the most common variant reported in North America and worldwide in the Genbank Database. Prior hamster data from the CDC with the Texas coyote 323R rabies isolate demonstrated 70-100% protection with the use of PEP (consisting of HRIG plus rabies vaccine) initiated 24 hours after viral challenge. In contrast, 100% of animals not treated, or treated with vaccine only, developed rabies, highlighting the severity of the viral challenge.

Figure 7A:
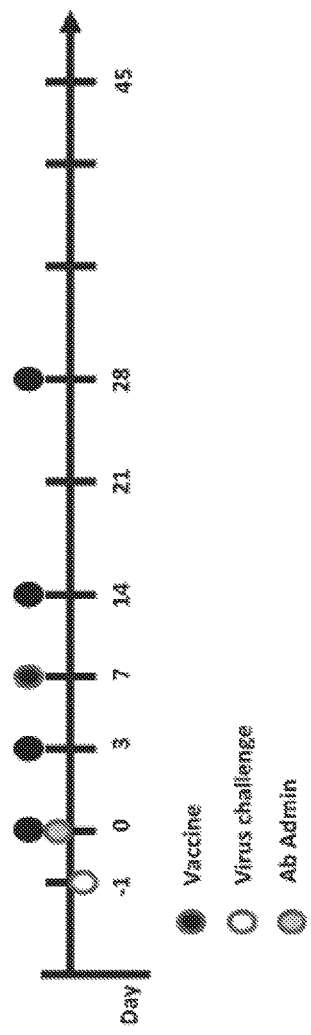
FIG. 7A shows the experimental design of the post-exposure prophylaxis (PEP) treatment study in a lethal challenge hamster model, with a schematic diagram showing a timeline for vaccine and antibody treatments (top) and a table showing test group and dosing information.

Data from the vaccine interference studies in uninfected hamsters (Example 11) were used to identify doses of R172 to examine in the PEP model. These R172 doses were evaluated in combination with rabies vaccine (IMOVAX®, Sanofi Pasteur) as post-exposure prophylaxis in the hamster challenge study (FIG. 7A).

Figure 7B:
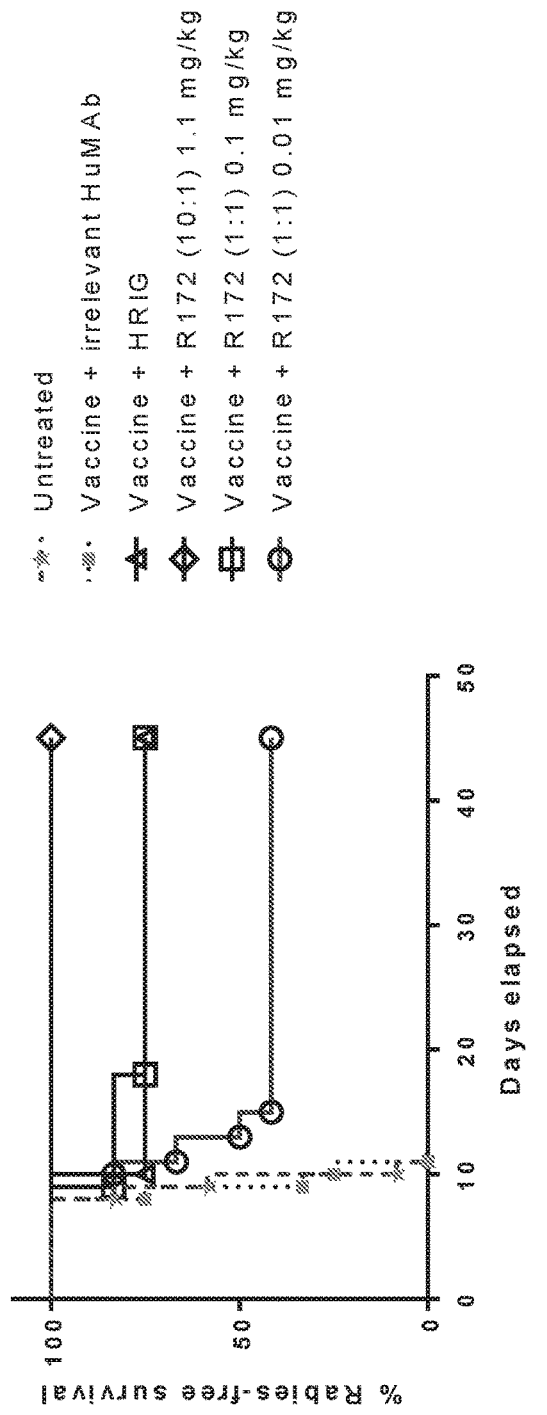
FIG. 7B is a survival curve showing the percentage of rabies-free survival over time for each test group in a PEP treatment study in which hamsters were challenged with $2.5 \times 10^3$ FFU of the rabies virus Texas coyote 323R.

Twelve female Syrian golden hamsters in each cohort were challenged with $2.5 \times 10^3$ FFU of the rabies virus Texas coyote 323R. In the untreated cohort and the cohort receiving irrelevant HuMAb plus vaccine, 100% mortality was observed (FIG. 7B). The median survival was 11 days for untreated animals and 10 days for those receiving vaccine and an irrelevant MAb. The cohort receiving the standard-of-care PEP regimen of 20 IU/kg of HRIG with vaccine had a 75% survival rate. Interestingly, R172-containing PEP regimens protected hamsters in a dose-dependent manner. All of the animals treated with R172 (17C7/2B10 10:1 ratio) at 1.1 mg/kg survived, 75% of the animals given R172 (17C7/2B10 1:1 ratio) at 0.1 mg/kg survived, and 42% of the animals who received 0.01 mg/kg of R172 (17C7/2B10 1:1 ratio) survived (FIG. 7B). All of the animals that died during the study were confirmed to have rabies virus.

The ability of the R172 mAb cocktail to protect hamsters exposed to a lethal rabies virus challenge was also evaluated using the bat rabies variant "3860 bat." The 3860 bat rabies virus was isolated from a *Pipistrellus hesperus* bat in Arizona and adapted to cell culture at the CDC. The 3860 bat isolate contains an "E33 N336 S346" epitope variant with a unique I338T mutation acquired during cell culture adaptation (CDC). The I338T mutation is located within antigenic site III and abrogates 17C7 neutralization in RFFIT; 2B10 retains activity against the I338T variant.

Figure 7C:
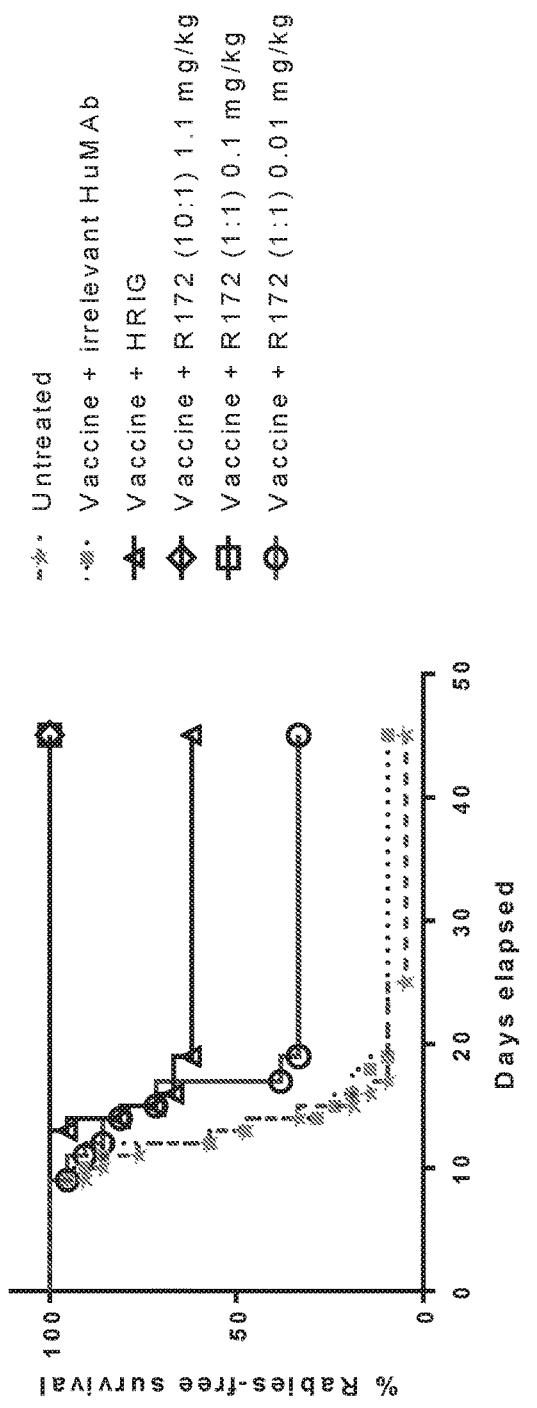
FIG. 7C is a survival curve showing the percentage of rabies-free survival over time for each test group in a PEP treatment study in which hamsters were challenged with $1.2 \times 10^4$ FFU of the bat rabies variant "3860 bat."

Twenty-one hamsters in each cohort were challenged with $1.2 \times 10^4$ FFU of the 3860 bat virus. In the untreated cohort, 5% of the animals survived, and in the cohort treated with irrelevant mAb plus rabies vaccine, 10% of the animals survived. The remainder of the animals in these cohorts developed rabies. The cohort receiving the standard-of-care PEP regimen of 20 IU/kg of HRIG with vaccine had a 62% survival rate. All animals treated with R172 (17C7/2B10 10:1 ratio) plus vaccine at 1.1 mg/kg survived, except for two animals that died from non-rabies related causes at late time points (days 35 (injury) and 40 (likely sepsis)). The brains from these two animals tested negative for rabies by DFA. All of the animals treated with R172 (17C7/2B10 1:1 ratio) plus vaccine at 0.1 mg/kg survived, and 33% of the animals who received 0.01 mg/kg of R172 (17C7/2B10 1:1 ratio) plus vaccine survived, while the remainder of the animals in this cohort developed rabies (FIG. 7C). Rabies infection was confirmed post-mortem in all animals who developed rabies. Given the resistance observed to 17C7 neutralization in vitro with the 3860 bat viral stock containing the I338T mutation, the in vivo protection from lethal challenge with the 3860 bat virus was likely provided by the 2B10 mAb.

In summary, these PEP experiments demonstrate that the R172 human monoclonal antibody cocktail was protective in an established hamster model of lethal rabies challenge. Treatment with R172 PEP regimens with 1.1 mg/kg R172 (10:1 ratio) and 0.1 mg/kg R172 (1:1 ratio) as the passive antibody component demonstrated 75-100% survival rates in the lethal challenge model, respectively, which was comparable to the 62-75% survival rate in the standard-of-care group receiving 20 IU/kg HRIG and vaccine. These in vivo animal data support use of the R172 monoclonal antibody cocktail as a potential PEP therapy for humans with exposures to suspected rabid animals.

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An antibody that specifically binds to rabies virus G protein, wherein the antibody comprises the following six complementarity determining regions (CDRs):
   (a) a CDR-H1 comprising the amino acid sequence of GFTFSYFAMH (SEQ ID NO: 1);
   (b) a CDR-H2 comprising the amino acid sequence of TIGTGGGTYYADSVKG (SEQ ID NO: 2);
   (c) a CDR-H3 comprising the amino acid sequence of CARDNALRSFDWLFYSFDY (SEQ ID NO: 3);
   (d) a CDR-L1 comprising the amino acid sequence of RASQSISSSYLA (SEQ ID NO: 4);
   (e) a CDR-L2 comprising the amino acid sequence of GASSRAT (SEQ ID NO: 5); and
   (f) a CDR-L3 comprising the amino acid sequence of QRYGSSYT (SEQ ID NO: 6).

2. The antibody of claim 1, wherein the antibody comprises (a) a heavy chain variable (VH) domain comprising a sequence having at least 90% sequence identity to the amino acid sequence of SEQ ID NO: 15 and (b) a light chain variable (VL) domain comprising a sequence having at least 90% sequence identity to the amino acid sequence of SEQ ID NO: 16.

3. The antibody of claim 1, wherein the antibody is monoclonal, human, humanized, or chimeric.

4. The antibody of claim 1, wherein the antibody is an antibody fragment that binds rabies virus G protein.

5. The antibody of claim 3, wherein the antibody fragment is selected from the group consisting of Fab, Fab'-SH, Fv, scFv, and (Fab')$_2$ fragments.

6. The antibody of claim 1, wherein the antibody is a full-length antibody.

7. The antibody of claim 6, wherein the full-length antibody comprises (a) a heavy chain sequence comprising at least 90% sequence identity to the amino acid sequence of SEQ ID NO: 17 and (b) a light chain sequence comprising at least 90% sequence identity to the amino acid sequence of SEQ ID NO: 18.

8. The antibody of claim 1, wherein the antibody binds to an epitope in antigenic site II of rabies virus G protein.

9. The antibody of claim 8, wherein the epitope comprises amino acid residue Glu33.

10. The antibody of claim 9, wherein the epitope further comprises amino acid residue Cys35.

11. A pharmaceutical composition comprising the antibody of claim 1.

12. The pharmaceutical composition of claim 11, further comprising a second antibody comprising the following six CDRs:
   (a) a CDR-H1 comprising the amino acid sequence of TYAMH (SEQ ID NO: 19);
   (b) a CDR-H2 comprising the amino acid sequence of VVSYDGRTKDYADSVKG (SEQ ID NO: 20);
   (c) a CDR-H3 comprising the amino acid sequence of ERFSGAYFDY (SEQ ID NO: 21);
   (d) a CDR-L1 comprising the amino acid sequence of RASQSVSSYLA (SEQ ID NO: 22);
   (e) a CDR-L2 comprising the amino acid sequence of DASNRAT (SEQ ID NO: 23); and
   (f) a CDR-L3 comprising the amino acid sequence of QQRNNWP (SEQ ID NO: 24).

13. The pharmaceutical composition of claim 12, wherein the second antibody comprises (a) a VH domain comprising a sequence having at least 90% sequence identity to the amino acid sequence of SEQ ID NO: 25 and (b) a VL domain comprising a sequence having at least 90% sequence identity to the amino acid sequence of SEQ ID NO: 26.

14. An isolated nucleic acid encoding the antibody of claim 1.

15. A vector comprising the nucleic acid of claim 14.

16. A host cell comprising the vector of claim 15.

17. A method of producing an antibody that specifically binds to rabies virus G protein, the method comprising culturing the host cell of claim 16 in a culture medium.

18. A method of treating a subject having a rabies virus infection comprising administering to the subject a therapeutically effective amount of the antibody of claim 1, thereby treating the subject.

19. A method of treating a subject at risk of developing a rabies virus infection comprising administering to the subject a therapeutically effective amount of the antibody of claim 1, thereby treating the subject.

20. The antibody of claim 1, wherein the antibody is an IgG antibody.

21. The antibody of claim 20, wherein the IgG antibody is an IgG1 antibody.

22. An antibody that specifically binds to rabies virus G protein, wherein the antibody comprises a VH domain comprising the amino acid sequence of SEQ ID NO: 15 and a VL domain comprising the amino acid sequence of SEQ ID NO: 16.

23. An antibody that specifically binds to rabies virus G protein, wherein the antibody comprises a heavy chain sequence comprising the amino acid sequence of SEQ ID NO: 17 and a light chain sequence comprising the amino acid sequence of SEQ ID NO: 18.

24. The pharmaceutical composition of claim 13, wherein the VH domain of the second antibody comprises the amino acid sequence of SEQ ID NO: 25 and the VL domain of the second antibody comprises the amino acid sequence of SEQ ID NO: 26.

25. The host cell of claim 16, wherein the host cell is a mammalian cell.

26. The host cell of claim 25, wherein the mammalian cell is a Chinese hamster ovary (CHO) cell.

27. The host cell of claim 16, wherein the host cell is a prokaryotic cell.

28. The host cell of claim 27, wherein the prokaryotic cell is an *E. coli* cell.

29. The method of claim 18, wherein the antibody is administered to the subject in a dosage of about 0.001 mg/kg to about 10 mg/kg.

30. The method of claim 19, wherein the antibody is administered to the subject in a dosage of about 0.001 mg/kg to about 10 mg/kg.

31. The method of claim 18, wherein the subject is administered at least one, at least two, at least three, at least four, or at least five doses of the antibody.

32. The method of claim 19, wherein the subject is administered at least one, at least two, at least three, at least four, or at least five doses of the antibody.

* * * * *

UNITED STATES PATENT AND TRADEMARK OFFICE
CERTIFICATE OF CORRECTION

PATENT NO. : 10,450,367 B2
APPLICATION NO. : 15/750716
DATED : October 22, 2019
INVENTOR(S) : William D. Thomas, Jr. et al.

It is certified that error appears in the above-identified patent and that said Letters Patent is hereby corrected as shown below:

In the Claims

Column 63, Line 44, replace "claim 3" with --claim 4--.

Signed and Sealed this
Fourth Day of February, 2020

Andrei Iancu
*Director of the United States Patent and Trademark Office*